(12) United States Patent
Vermeere et al.

(10) Patent No.: US 8,353,812 B2
(45) Date of Patent: Jan. 15, 2013

(54) HANDHELD RADIATION DELIVERY SYSTEM

(75) Inventors: Bill Vermeere, Portola Valley, CA (US); William Metzger, San Diego, CA (US); Jay Daulton, Gilroy, CA (US); Benjamin Woodward, Santa Clara, CA (US); Mark Diel, Menlo Park, CA (US); David Beaulieu, Berkeley, CA (US); Kristopher Konawalik, San Francisco, CA (US); Christopher Kelly, Larkspur, CA (US); Guang Gun (Max) Chen, San Francisco, CA (US)

(73) Assignee: NeoVista, Inc., Newark, CA (US)

( * ) Notice: Subject to any disclaimer, the term of this patent is extended or adjusted under 35 U.S.C. 154(b) by 896 days.

(21) Appl. No.: 12/477,228

(22) Filed: Jun. 3, 2009

(65) Prior Publication Data

US 2010/0030010 A1 Feb. 4, 2010

Related U.S. Application Data

(60) Provisional application No. 61/058,737, filed on Jun. 4, 2008.

(51) Int. Cl.
*A61N 5/00* (2006.01)
(52) U.S. Cl. .......................................................... 600/1
(58) Field of Classification Search .................. 600/9–15
See application file for complete search history.

(56) References Cited

U.S. PATENT DOCUMENTS

| 839,061 A | 12/1906 | Farjas |
|---|---|---|
| 2,517,568 A | 9/1948 | Hissong |
| 2,559,793 A | 7/1951 | Pregel |
| 4,198,570 A | 4/1980 | McHugh et al. |
| 4,200,804 A | 4/1980 | Farella et al. |
| 4,584,991 A | 4/1986 | Tokita et al. |
| 4,627,420 A | 12/1986 | Katz |
| 4,662,869 A | 5/1987 | Wright |
| 4,699,614 A | 10/1987 | Glazier |
| 4,705,955 A | 11/1987 | Mileikowsky |
| 4,846,172 A | 7/1989 | Berlin |
| 4,846,808 A | 7/1989 | Haber et al. |
| 4,861,520 A | 8/1989 | Van't Hooft et al. |
| 4,883,446 A | 11/1989 | Glazier |
| 4,891,165 A | 1/1990 | Suthanthiran |

(Continued)

FOREIGN PATENT DOCUMENTS

DE 19933284 1/2001

(Continued)

OTHER PUBLICATIONS

Int. Appln. No. PCT/US 2009/046118: International Search Report and Written Opinion of the International Searching Authority Aug. 27, 2009.

(Continued)

*Primary Examiner* — John Lacyk
(74) *Attorney, Agent, or Firm* — Cook Alex Ltd.

(57) ABSTRACT

A handheld radiation delivery system is disclosed that includes a two-part delivery module comprising a reusable portion that contains a radioactive source wire and a disposable portion that includes a drive assembly for moving the radioactive source wire between storage and treatment positions. A disposable applicator tip is provided that includes a cannula for receiving the radioactive source wire when in the treatment position and a mechanism for limiting the number of uses of the device. A handheld cable actuator is operatively connected to the disposable portion of the handpiece to impart motion to the source wire.

41 Claims, 20 Drawing Sheets

U.S. PATENT DOCUMENTS

| | | |
|---|---|---|
| 4,897,076 A | 1/1990 | Puthawala et al. |
| 4,908,020 A | 3/1990 | Pettersen |
| 4,921,327 A | 5/1990 | Zito |
| 4,957,223 A | 9/1990 | Beilush |
| 4,957,476 A | 9/1990 | Cano |
| 4,969,863 A | 11/1990 | Van't Hooft et al. |
| 4,973,308 A | 11/1990 | Borras et al. |
| 4,994,012 A | 2/1991 | Nakayama et al. |
| 4,996,159 A | 2/1991 | Glaser |
| 5,080,648 A | 1/1992 | D'Antonio |
| 5,084,001 A | 1/1992 | Van'tHooft et al. |
| 5,089,000 A | 2/1992 | Agee et al. |
| 5,106,370 A | 4/1992 | Stewart |
| 5,123,902 A | 6/1992 | Muller et al. |
| 5,129,895 A | 7/1992 | Vassiliadis et al. |
| 5,141,487 A | 8/1992 | Liprie |
| 5,147,282 A | 9/1992 | Kan |
| 5,147,295 A | 9/1992 | Stewart |
| 5,149,323 A | 9/1992 | Colonna |
| 5,183,455 A | 2/1993 | Hayman et al. |
| 5,195,975 A | 3/1993 | Castagna |
| 5,199,939 A | 4/1993 | Dake et al. |
| 5,201,726 A | 4/1993 | Kirkham |
| 5,203,353 A | 4/1993 | Easley et al. |
| 5,257,988 A | 11/1993 | L'Esperance, Jr. |
| 5,261,891 A | 11/1993 | Brinkerhoff et al. |
| 5,267,960 A | 12/1993 | Hayman et al. |
| 5,275,593 A | 1/1994 | Easley et al. |
| 5,281,197 A | 1/1994 | Arias et al. |
| 5,282,781 A | 2/1994 | Liprie |
| 5,284,479 A | 2/1994 | deJong |
| 5,290,585 A | 3/1994 | Elton |
| 5,312,333 A | 5/1994 | Churinetz et al. |
| 5,322,499 A | 6/1994 | Liprie |
| 5,342,283 A | 8/1994 | Good |
| 5,350,355 A | 9/1994 | Sklar |
| 5,350,356 A | 9/1994 | Bales et al. |
| 5,354,257 A | 10/1994 | Roubin et al. |
| 5,415,631 A | 5/1995 | Churinetz et al. |
| 5,417,709 A | 5/1995 | Slater |
| 5,422,926 A | 6/1995 | Smith et al. |
| 5,425,730 A | 6/1995 | Luloh |
| 5,426,662 A | 6/1995 | Mefferd et al. |
| 5,431,907 A | 7/1995 | Abelson et al. |
| 5,487,725 A | 1/1996 | Peyman |
| 5,503,613 A | 4/1996 | Weinberger |
| 5,503,614 A | 4/1996 | Liprie |
| 5,528,651 A | 6/1996 | Leksell et al. |
| 5,533,521 A | 7/1996 | Granger |
| 5,549,554 A | 8/1996 | Miraki |
| 5,556,389 A | 9/1996 | Liprie |
| 5,569,160 A | 10/1996 | Sauer et al. |
| 5,570,408 A | 10/1996 | Gibson |
| 5,575,749 A | 11/1996 | Liprie |
| 5,575,777 A | 11/1996 | Cover et al. |
| 5,595,270 A | 1/1997 | Braun et al. |
| 5,596,011 A | 1/1997 | Repine et al. |
| 5,613,949 A | 3/1997 | Miraki |
| 5,618,266 A | 4/1997 | Liprie |
| 5,620,456 A | 4/1997 | Sauer et al. |
| 5,624,372 A | 4/1997 | Liprie |
| 5,624,406 A | 4/1997 | Labouze |
| 5,624,437 A | 4/1997 | Freeman et al. |
| 5,637,073 A | 6/1997 | Freire |
| 5,651,783 A | 7/1997 | Reynard |
| 5,688,220 A | 11/1997 | Verin et al. |
| 5,702,367 A | 12/1997 | Cover et al. |
| 5,707,332 A | 1/1998 | Weinberger |
| 5,713,828 A | 2/1998 | Coniglione |
| 5,716,317 A | 2/1998 | Okano et al. |
| 5,722,951 A | 3/1998 | Marano |
| 5,728,042 A | 3/1998 | Schwager |
| 5,729,583 A | 3/1998 | Tang et al. |
| 5,738,677 A | 4/1998 | Colvard et al. |
| 5,772,642 A | 6/1998 | Ciamacco, Jr. et al. |
| 5,782,740 A | 7/1998 | Schneiderman |
| 5,792,098 A | 8/1998 | Felix et al. |
| 5,797,889 A | 8/1998 | Steinman |
| 5,807,231 A | 9/1998 | Liprie |
| 5,830,173 A | 11/1998 | Avery et al. |
| 5,833,593 A | 11/1998 | Liprie |
| 5,836,882 A | 11/1998 | Frazin |
| 5,843,115 A | 12/1998 | Morejon |
| 5,851,172 A | 12/1998 | Bueche et al. |
| 5,854,822 A | 12/1998 | Chornenky et al. |
| 5,855,546 A | 1/1999 | Hastings et al. |
| 5,857,956 A | 1/1999 | Liprie |
| 5,860,909 A | 1/1999 | Mick et al. |
| 5,863,284 A | 1/1999 | Klein |
| 5,865,720 A | 2/1999 | Hastings et al. |
| 5,865,806 A | 2/1999 | Howell |
| 5,868,785 A | 2/1999 | Tal et al. |
| 5,882,291 A | 3/1999 | Bradshaw et al. |
| 5,885,279 A | 3/1999 | Bretton |
| 5,899,882 A | 5/1999 | Waksman et al. |
| 5,904,144 A | 5/1999 | Hamming et al. |
| 5,913,813 A | 6/1999 | Williams et al. |
| 5,924,974 A | 7/1999 | Loffler |
| 5,928,130 A | 7/1999 | Schmidt |
| 5,947,958 A | 9/1999 | Woodard et al. |
| 5,957,829 A | 9/1999 | Thornton |
| 5,976,106 A | 11/1999 | Verin et al. |
| 5,984,853 A | 11/1999 | Smith |
| 6,004,269 A | 12/1999 | Crowley et al. |
| 6,004,279 A | 12/1999 | Crowley et al. |
| 6,007,474 A | 12/1999 | Rydell |
| 6,013,056 A | 1/2000 | Pettersen |
| 6,019,718 A | 2/2000 | Hektner |
| 6,022,324 A | 2/2000 | Skinner |
| 6,024,690 A | 2/2000 | Lee et al. |
| 6,030,333 A | 2/2000 | Sioshansi et al. |
| 6,033,357 A | 3/2000 | Ciezki et al. |
| 6,036,631 A | 3/2000 | McGrath et al. |
| 6,041,252 A | 3/2000 | Walker et al. |
| 6,047,861 A | 4/2000 | Vidal et al. |
| 6,048,300 A | 4/2000 | Thornton et al. |
| 6,050,930 A | 4/2000 | Teirstein |
| 6,053,858 A | 4/2000 | Bueche et al. |
| 6,059,713 A | 5/2000 | Urick et al. |
| 6,059,752 A | 5/2000 | Segal |
| 6,059,828 A | 5/2000 | Peyman |
| 6,063,050 A | 5/2000 | Manna et al. |
| 6,069,938 A | 5/2000 | Chornenky et al. |
| 6,071,227 A | 6/2000 | Popowski et al. |
| 6,074,338 A | 6/2000 | Popowski et al. |
| 6,079,868 A | 6/2000 | Rydell |
| 6,083,200 A | 7/2000 | Grimm et al. |
| 6,090,078 A | 7/2000 | Erskine |
| 6,093,142 A | 7/2000 | Ciamacco, Jr. |
| 6,095,966 A | 8/2000 | Chornenky et al. |
| 6,099,457 A | 8/2000 | Good |
| 6,099,499 A | 8/2000 | Ciamacco, Jr. |
| 6,102,844 A | 8/2000 | Ravins et al. |
| 6,106,454 A | 8/2000 | Berg et al. |
| 6,108,402 A | 8/2000 | Chornenky |
| 6,110,097 A | 8/2000 | Hastings et al. |
| 6,111,932 A | 8/2000 | Dinsmore |
| 6,117,065 A | 9/2000 | Hastings et al. |
| 6,117,480 A | 9/2000 | Spallek et al. |
| 6,120,479 A | 9/2000 | Campbell et al. |
| 6,132,358 A | 10/2000 | Glenn et al. |
| 6,134,294 A | 10/2000 | Gibbs |
| 6,142,994 A | 11/2000 | Swanson et al. |
| 6,146,322 A | 11/2000 | Papirov et al. |
| 6,149,574 A | 11/2000 | Trauthen et al. |
| 6,149,931 A | 11/2000 | Schwartz et al. |
| 6,159,139 A | 12/2000 | Chiu |
| 6,159,140 A | 12/2000 | Loeffler et al. |
| 6,159,144 A | 12/2000 | Angel et al. |
| 6,162,165 A | 12/2000 | Apple et al. |
| 6,162,198 A | 12/2000 | Coffey et al. |
| 6,163,947 A | 12/2000 | Coniglione |
| 6,164,281 A | 12/2000 | Zhao |
| 6,165,153 A | 12/2000 | Kashmer |
| 6,175,760 B1 | 1/2001 | Baskin et al. |
| 6,179,262 B1 | 1/2001 | Ellard et al. |
| 6,179,768 B1 | 1/2001 | Loffler et al. |

| Patent No. | Date | Inventor(s) |
|---|---|---|
| 6,181,770 B1 | 1/2001 | Ciravolo et al. |
| RE37,047 E | 2/2001 | Py |
| 6,183,410 B1 | 2/2001 | Jacobsen et al. |
| 6,190,303 B1 | 2/2001 | Glenn et al. |
| 6,190,350 B1 | 2/2001 | Davis et al. |
| 6,195,411 B1 | 2/2001 | Dinsmore |
| 6,196,963 B1 | 3/2001 | Williams |
| 6,197,001 B1 | 3/2001 | Wilson et al. |
| 6,198,804 B1 | 3/2001 | Dinsmore |
| 6,203,524 B1 | 3/2001 | Burney et al. |
| 6,210,312 B1 | 4/2001 | Nagy |
| 6,210,315 B1 | 4/2001 | Andrews et al. |
| 6,213,932 B1 | 4/2001 | Schmidt |
| 6,221,003 B1 | 4/2001 | Sierocuk et al. |
| 6,224,536 B1 | 5/2001 | Pike |
| 6,231,494 B1 | 5/2001 | Verin et al. |
| 6,231,591 B1 | 5/2001 | Desai |
| 6,234,951 B1 | 5/2001 | Hastings |
| 6,238,332 B1 | 5/2001 | Kanesaka |
| 6,241,651 B1 | 6/2001 | Smith et al. |
| 6,245,047 B1 | 6/2001 | Feda et al. |
| 6,248,092 B1 | 6/2001 | Miraki et al. |
| 6,258,019 B1 | 7/2001 | Verin et al. |
| 6,261,320 B1 | 7/2001 | Tam et al. |
| 6,264,599 B1 | 7/2001 | Slater et al. |
| 6,267,718 B1 | 7/2001 | Vitali et al. |
| 6,270,472 B1 | 8/2001 | Antaki et al. |
| 6,273,850 B1 | 8/2001 | Gambale et al. |
| 6,280,407 B1 | 8/2001 | Manna et al. |
| 6,283,910 B1 | 9/2001 | Bradshaw et al. |
| 6,283,911 B1 | 9/2001 | Keren |
| 6,283,941 B1 | 9/2001 | Schoenfeld et al. |
| 6,284,751 B1 | 9/2001 | Aiello et al. |
| 6,285,735 B1 | 9/2001 | Sliski et al. |
| 6,289,079 B1 | 9/2001 | Chornenky et al. |
| 6,290,656 B1 | 9/2001 | Boyle et al. |
| 6,293,899 B1 | 9/2001 | Sioshansi et al. |
| 6,299,054 B1 | 10/2001 | Gibbs, Jr. |
| 6,301,328 B1 | 10/2001 | Sliski et al. |
| 6,302,581 B1 | 10/2001 | Sliski et al. |
| 6,306,074 B1 | 10/2001 | Waksman et al. |
| 6,312,374 B1 | 11/2001 | von Hoffmann |
| 6,312,393 B1 | 11/2001 | Abreu |
| 6,319,273 B1 | 11/2001 | Chen et al. |
| 6,320,932 B2 | 11/2001 | Dinsmore |
| 6,320,935 B1 | 11/2001 | Shinar et al. |
| 6,338,709 B1 | 1/2002 | Geoffrion et al. |
| 6,347,244 B1 | 2/2002 | Dubnack |
| 6,350,227 B1 | 2/2002 | Shikhman et al. |
| 6,352,501 B1 | 3/2002 | Urick |
| 6,354,989 B1 | 3/2002 | Nudeshima |
| 6,359,963 B1 | 3/2002 | Cash |
| 6,361,487 B1 | 3/2002 | Green et al. |
| 6,377,846 B1 | 4/2002 | Chornenky et al. |
| 6,378,526 B1 | 4/2002 | Bowman et al. |
| 6,387,035 B1 | 5/2002 | Jung, Jr. et al. |
| 6,391,026 B1 | 5/2002 | Hung et al. |
| 6,395,294 B1 | 5/2002 | Peyman |
| 6,397,849 B1 | 6/2002 | Bowman et al. |
| 6,398,708 B1 | 6/2002 | Hastings et al. |
| 6,398,743 B1 | 6/2002 | Halseth et al. |
| 6,402,676 B2 | 6/2002 | Peterson |
| 6,409,651 B1 | 6/2002 | Brown, III |
| 6,409,943 B1 | 6/2002 | Lavie et al. |
| 6,413,204 B1 | 7/2002 | Winkler et al. |
| 6,415,016 B1 | 7/2002 | Chornenky et al. |
| 6,416,457 B1 | 7/2002 | Urick et al. |
| 6,419,621 B1 | 7/2002 | Sioshansi et al. |
| 6,421,416 B1 | 7/2002 | Sliski et al. |
| 6,422,989 B1 | 7/2002 | Hektner |
| 6,425,895 B1 | 7/2002 | Swanson et al. |
| 6,428,463 B1 | 8/2002 | Ravins et al. |
| 6,428,468 B1 | 8/2002 | Knighton et al. |
| 6,432,035 B1 | 8/2002 | Ravins et al. |
| 6,433,012 B1 | 8/2002 | Tuse et al. |
| 6,436,026 B1 | 8/2002 | Sioshansi et al. |
| 6,438,206 B1 | 8/2002 | Shinar et al. |
| 6,442,822 B1 | 9/2002 | Liprie |
| 6,443,881 B1 | 9/2002 | Finger |
| 6,443,976 B1 | 9/2002 | Flower et al. |
| 6,450,937 B1 | 9/2002 | Mercereau et al. |
| 6,450,938 B1 | 9/2002 | Miller |
| 6,458,068 B1 | 10/2002 | Ellard et al. |
| 6,458,069 B1 | 10/2002 | Tam et al. |
| 6,464,626 B1 | 10/2002 | Peterson |
| 6,465,954 B1 | 10/2002 | Kerslick et al. |
| 6,471,630 B1 | 10/2002 | Sioshansi et al. |
| 6,471,636 B1 | 10/2002 | Sano et al. |
| 6,473,491 B2 | 10/2002 | Chornenky et al. |
| 6,480,567 B1 | 11/2002 | Feda et al. |
| 6,482,142 B1 | 11/2002 | Winkler et al. |
| 6,485,406 B1 | 11/2002 | Ziegler et al. |
| 6,491,619 B1 | 12/2002 | Trauthen et al. |
| 6,496,561 B1 | 12/2002 | Meyer et al. |
| 6,497,645 B1 | 12/2002 | Halpern |
| 6,506,144 B1 | 1/2003 | Gilan |
| 6,506,145 B1 | 1/2003 | Bradshaw et al. |
| 6,508,755 B1 | 1/2003 | Ravins et al. |
| 6,508,764 B1 | 1/2003 | Thiele et al. |
| 6,508,781 B1 | 1/2003 | Brennan et al. |
| 6,512,942 B1 | 1/2003 | Burdette et al. |
| 6,514,192 B2 | 2/2003 | Tiren |
| 6,514,193 B2 | 2/2003 | Kaplan |
| 6,530,875 B1 | 3/2003 | Taylor et al. |
| 6,546,077 B2 | 4/2003 | Chornenky et al. |
| 6,551,291 B1 | 4/2003 | de Juan, Jr. et al. |
| 6,558,309 B2 | 5/2003 | Hogendijk et al. |
| 6,558,402 B1 | 5/2003 | Chelak et al. |
| 6,560,312 B2 | 5/2003 | Cash |
| 6,561,967 B2 | 5/2003 | Schmidt |
| 6,572,527 B2 | 6/2003 | Steele, Sr. et al. |
| 6,575,888 B2 | 6/2003 | Zamora et al. |
| 6,575,890 B2 | 6/2003 | Bellofatto et al. |
| 6,579,256 B2 | 6/2003 | Hughes |
| 6,582,417 B1 | 6/2003 | Ledesma et al. |
| 6,585,633 B2 | 7/2003 | Vitali et al. |
| 6,585,696 B2 | 7/2003 | Petersen et al. |
| 6,589,157 B2 | 7/2003 | Fontayne et al. |
| 6,589,158 B2 | 7/2003 | Winkler |
| 6,592,508 B1 | 7/2003 | Ravins et al. |
| 6,599,232 B2 | 7/2003 | Joachim et al. |
| 6,607,478 B2 | 8/2003 | Williams |
| 6,607,512 B2 | 8/2003 | Oliver et al. |
| 6,616,594 B2 | 9/2003 | Fontayne et al. |
| 6,623,418 B2 | 9/2003 | Smith |
| 6,626,817 B2 | 9/2003 | Luth |
| 6,626,855 B2 | 9/2003 | Weng et al. |
| 6,629,960 B2 | 10/2003 | Fontayne |
| 6,632,176 B2 | 10/2003 | McIntire et al. |
| 6,635,008 B1 | 10/2003 | Liprie |
| 6,638,205 B1 | 10/2003 | Chan et al. |
| 6,641,519 B2 | 11/2003 | Kindlein et al. |
| 6,648,811 B2 | 11/2003 | Sierocuk et al. |
| 6,656,107 B1 | 12/2003 | Pedersen et al. |
| 6,659,933 B2 | 12/2003 | Asano |
| 6,676,590 B1 | 1/2004 | Urick et al. |
| 6,676,607 B2 | 1/2004 | DeJuan, Jr. et al. |
| 6,682,471 B2 | 1/2004 | Steele, Sr. et al. |
| 6,685,618 B2 | 2/2004 | Tam et al. |
| 6,689,043 B1 | 2/2004 | McIntire et al. |
| 6,692,759 B1 | 2/2004 | Wong et al. |
| 6,702,784 B1 | 3/2004 | Sheckler et al. |
| 6,712,782 B2 | 3/2004 | Ford |
| 6,714,620 B2 | 3/2004 | Caflisch et al. |
| 6,719,750 B2 | 4/2004 | Varner et al. |
| 6,726,617 B1 | 4/2004 | Schmidt |
| 6,749,553 B2 | 6/2004 | Brauckman et al. |
| 6,752,753 B1 | 6/2004 | Hoskins et al. |
| 6,755,775 B2 | 6/2004 | Kalas et al. |
| 6,755,776 B1 | 6/2004 | Granados |
| 6,770,019 B2 | 8/2004 | Fritz et al. |
| 6,771,737 B2 | 8/2004 | Kerslick et al. |
| 6,779,715 B2 | 8/2004 | Williams |
| 6,786,865 B2 | 9/2004 | Dhindsa |
| 6,786,875 B2 | 9/2004 | Barker et al. |
| 6,790,170 B2 | 9/2004 | Moody |
| 6,790,197 B2 | 9/2004 | Kosinski et al. |
| 6,792,306 B2 | 9/2004 | Henley et al. |

| | | |
|---|---|---|
| 6,796,935 B1 | 9/2004 | Savino |
| 6,799,075 B1 | 9/2004 | Chornenky et al. |
| 6,802,824 B2 | 10/2004 | Mickley et al. |
| 6,810,109 B2 | 10/2004 | Chornenky |
| 6,837,865 B2 | 1/2005 | Kneer |
| 6,866,624 B2 | 3/2005 | Chornenky et al. |
| 6,875,165 B2 | 4/2005 | de Juan, Jr. et al. |
| 6,893,441 B2 | 5/2005 | Brommersma et al. |
| 6,899,683 B2 | 5/2005 | Mault et al. |
| 6,899,717 B2 | 5/2005 | Weber et al. |
| 6,914,960 B2 | 7/2005 | Swanson et al. |
| 6,932,803 B2 | 8/2005 | Newby |
| 6,941,950 B2 | 9/2005 | Wilson et al. |
| 6,949,064 B2 | 9/2005 | Lowery et al. |
| 6,964,648 B2 | 11/2005 | Talling et al. |
| 6,976,968 B2 | 12/2005 | Ritchart et al. |
| 6,985,557 B2 | 1/2006 | Jaafar |
| 6,986,756 B2 | 1/2006 | Pelkey et al. |
| 6,989,543 B2 | 1/2006 | Drobnik et al. |
| 6,991,618 B2 | 1/2006 | Lau et al. |
| 7,041,047 B2 | 5/2006 | Gellman et al. |
| 7,041,048 B2 | 5/2006 | Drobnik et al. |
| 7,041,085 B2 | 5/2006 | Perez et al. |
| 7,052,482 B2 | 5/2006 | Lau et al. |
| 7,070,554 B2 | 7/2006 | White et al. |
| 7,083,596 B2 | 8/2006 | Saied |
| 7,090,681 B2 | 8/2006 | Weber et al. |
| 7,131,942 B2 | 11/2006 | Taylor et al. |
| 7,144,378 B2 | 12/2006 | Arnott |
| 7,147,644 B2 | 12/2006 | Weber et al. |
| 7,153,276 B2 | 12/2006 | Barker et al. |
| 7,175,642 B2 | 2/2007 | Briggs et al. |
| 7,179,912 B2 | 2/2007 | Halbrook et al. |
| 7,194,847 B2 | 3/2007 | Summons et al. |
| 7,199,375 B2 | 4/2007 | Drobnik et al. |
| 7,201,715 B2 | 4/2007 | Burdette et al. |
| 7,214,206 B2 | 5/2007 | Rue et al. |
| 7,217,255 B2 | 5/2007 | Boyle et al. |
| 7,220,225 B2 | 5/2007 | Dejuan, Jr. et al. |
| 7,223,225 B2 | 5/2007 | DeJuan, Jr. et al. |
| 7,223,226 B2 | 5/2007 | Biscotti |
| 7,232,408 B1 | 6/2007 | Fritz et al. |
| 7,247,160 B2 | 7/2007 | Seiler et al. |
| 7,273,445 B2 | 9/2007 | Pulido et al. |
| 7,276,019 B2 | 10/2007 | DeJuan, Jr. et al. |
| 7,291,117 B2 | 11/2007 | Boecker et al. |
| 7,294,118 B2 | 11/2007 | Saulenas et al. |
| 7,312,556 B2 | 12/2007 | Tahara et al. |
| 7,331,931 B2 | 2/2008 | Freeman et al. |
| 7,331,934 B2 | 2/2008 | Suresh et al. |
| 7,331,935 B2 | 2/2008 | Barere |
| 7,335,155 B2 | 2/2008 | Chu |
| 7,341,554 B2 | 3/2008 | Sekine et al. |
| 7,351,193 B2 | 4/2008 | Forman et al. |
| 7,351,227 B2 | 4/2008 | Lerner |
| 7,374,544 B2 | 5/2008 | Freeman et al. |
| 7,377,904 B2 | 5/2008 | Conway et al. |
| 7,396,341 B2 | 7/2008 | Schyra et al. |
| 7,407,495 B2 | 8/2008 | Barere et al. |
| 7,425,195 B2 | 9/2008 | Wissman et al. |
| 7,452,324 B2 | 11/2008 | Besing |
| 7,458,940 B2 | 12/2008 | Miller |
| 7,468,065 B2 | 12/2008 | Weber et al. |
| 7,481,776 B2 | 1/2009 | Boecker et al. |
| 7,485,128 B2 | 2/2009 | Boecker et al. |
| 7,488,305 B2 | 2/2009 | Mickley et al. |
| 7,491,178 B2 | 2/2009 | Boecker et al. |
| 7,496,174 B2 | 2/2009 | Gertner et al. |
| 7,497,862 B2 | 3/2009 | Viola |
| 7,500,966 B2 | 3/2009 | Hommann |
| 7,510,549 B2 | 3/2009 | Rue |
| 2001/0002427 A1 | 5/2001 | Verin et al. |
| 2001/0009970 A1 | 7/2001 | Chornenky et al. |
| 2001/0016027 A1 | 8/2001 | Dinsmore |
| 2001/0021382 A1 | 9/2001 | Ferrara et al. |
| 2001/0027261 A1 | 10/2001 | Ciezki et al. |
| 2001/0036955 A1 | 11/2001 | Gerritsen et al. |
| 2001/0050971 A1 | 12/2001 | Feda et al. |
| 2002/0013572 A1 | 1/2002 | Berlin |
| 2002/0015957 A1 | 2/2002 | Hageman et al. |
| 2002/0021784 A1 | 2/2002 | Chornenky et al. |
| 2002/0040015 A1 | 4/2002 | Miller et al. |
| 2002/0049247 A1 | 4/2002 | Chen |
| 2002/0054664 A1 | 5/2002 | Tiren |
| 2002/0054665 A1 | 5/2002 | Tiren |
| 2002/0055666 A1 | 5/2002 | Hunter et al. |
| 2002/0065448 A1 | 5/2002 | Bradshaw et al. |
| 2002/0072494 A1 | 6/2002 | Cao |
| 2002/0090053 A1 | 7/2002 | Chornenky et al. |
| 2002/0099255 A1 | 7/2002 | Liprie et al. |
| 2002/0106055 A1 | 8/2002 | Cash |
| 2002/0110220 A1 | 8/2002 | Shen et al. |
| 2002/0115902 A1 | 8/2002 | DeJuan, Jr. et al. |
| 2002/0146090 A1 | 10/2002 | Chornenky et al. |
| 2002/0156003 A1 | 10/2002 | Lorens et al. |
| 2002/0160954 A1 | 10/2002 | Hageman et al. |
| 2002/0160979 A1 | 10/2002 | Banerjee et al. |
| 2002/0172829 A1 | 11/2002 | Mori et al. |
| 2002/0183253 A1 | 12/2002 | Brazzell et al. |
| 2002/0183302 A1 | 12/2002 | Strong et al. |
| 2002/0193326 A1 | 12/2002 | Sukhatme |
| 2002/0193656 A1 | 12/2002 | Ravins et al. |
| 2003/0014092 A1 | 1/2003 | Neuhann |
| 2003/0105407 A1 | 6/2003 | Pearce, Jr. et al. |
| 2003/0144570 A1 | 7/2003 | Hunter et al. |
| 2003/0179854 A1 | 9/2003 | Jaafar |
| 2003/0199902 A1 | 10/2003 | Boecker et al. |
| 2003/0204125 A1 | 10/2003 | Brauckman et al. |
| 2003/0208096 A1 | 11/2003 | Tam et al. |
| 2003/0222228 A1 | 12/2003 | Chen Fu et al. |
| 2004/0116767 A1 | 6/2004 | Lebovic et al. |
| 2004/0116854 A1 | 6/2004 | Abulhaj et al. |
| 2004/0116909 A1 | 6/2004 | Neuberger et al. |
| 2004/0127819 A1 | 7/2004 | Roe |
| 2004/0158150 A1 | 8/2004 | Rabiner et al. |
| 2004/0162459 A1 | 8/2004 | Liprie et al. |
| 2004/0218721 A1 | 11/2004 | Chornenky et al. |
| 2004/0218724 A1 | 11/2004 | Chornenky et al. |
| 2004/0225175 A1 | 11/2004 | Moody et al. |
| 2005/0038394 A1 | 2/2005 | Schwarzbich |
| 2005/0131386 A1 | 6/2005 | Freeman et al. |
| 2005/0149017 A1 | 7/2005 | Dycus |
| 2005/0165403 A1 | 7/2005 | Miller |
| 2005/0177019 A1 | 8/2005 | DeJuan, Jr. et al. |
| 2005/0187518 A1 | 8/2005 | Pelkey et al. |
| 2005/0203439 A1 | 9/2005 | Heske et al. |
| 2005/0209553 A1 | 9/2005 | Landau |
| 2005/0209554 A1 | 9/2005 | Landau |
| 2005/0234424 A1 | 10/2005 | Besing et al. |
| 2005/0240168 A1 | 10/2005 | Neuberger et al. |
| 2005/0256361 A1 | 11/2005 | Mathieu et al. |
| 2005/0256362 A1 | 11/2005 | Mick et al. |
| 2005/0256529 A1 | 11/2005 | Yawata et al. |
| 2005/0261540 A1 | 11/2005 | Dischino et al. |
| 2005/0267319 A1 | 12/2005 | White et al. |
| 2005/0277802 A1 | 12/2005 | Larsen et al. |
| 2005/0288607 A1 | 12/2005 | Konrad |
| 2006/0025800 A1 | 2/2006 | Suresh |
| 2006/0041243 A1 | 2/2006 | Nayak et al. |
| 2006/0063961 A1 | 3/2006 | Drobnik et al. |
| 2006/0076023 A1 | 4/2006 | Rapacki et al. |
| 2006/0142629 A1 | 6/2006 | DeJuan et al. |
| 2006/0167403 A1 | 7/2006 | Henley et al. |
| 2006/0189838 A1 | 8/2006 | DeJuan et al. |
| 2006/0195044 A1 | 8/2006 | Cooke et al. |
| 2006/0204535 A1 | 9/2006 | Johnson |
| 2006/0229599 A1 | 10/2006 | Rashidi |
| 2006/0229641 A1 | 10/2006 | Gupta et al. |
| 2006/0235365 A1 | 10/2006 | Terwilliger et al. |
| 2006/0276680 A1 | 12/2006 | Seiler et al. |
| 2007/0010746 A1 | 1/2007 | Forman et al. |
| 2007/0032723 A1 | 2/2007 | Glossop |
| 2007/0043305 A1 | 2/2007 | Boecker et al. |
| 2007/0049863 A1 | 3/2007 | Jahns et al. |
| 2007/0055174 A1 | 3/2007 | Freeman et al. |
| 2007/0088245 A1 | 4/2007 | Babaev et al. |
| 2007/0123797 A1 | 5/2007 | Krause |
| 2007/0167873 A1 | 7/2007 | Freeman |

| | | | |
|---|---|---|---|
| 2007/0167874 A1 | 7/2007 | Freeman et al. | |
| 2007/0167875 A1 | 7/2007 | Freeman et al. | |
| 2007/0173742 A1 | 7/2007 | Freeman et al. | |
| 2007/0173743 A1 | 7/2007 | Freeman et al. | |
| 2007/0185412 A1 | 8/2007 | Boecker et al. | |
| 2007/0191667 A1 | 8/2007 | Lubock et al. | |
| 2007/0191737 A1 | 8/2007 | Freeman et al. | |
| 2007/0213601 A1 | 9/2007 | Freeman et al. | |
| 2007/0219462 A1 | 9/2007 | Briggs et al. | |
| 2007/0219463 A1 | 9/2007 | Briggs et al. | |
| 2007/0239103 A1 | 10/2007 | Hardin et al. | |
| 2007/0244425 A1 | 10/2007 | Pond | |
| 2007/0265485 A1 | 11/2007 | DeJuan, Jr. et al. | |
| 2007/0265487 A1 | 11/2007 | Lamoureux et al. | |
| 2007/0265488 A1 | 11/2007 | Lamoureux et al. | |
| 2008/0004483 A1 | 1/2008 | Tarone et al. | |
| 2008/0009659 A1 | 1/2008 | Smith et al. | |
| 2008/0009661 A1 | 1/2008 | Lamoureux et al. | |
| 2008/0015660 A1 | 1/2008 | Herekar | |
| 2008/0021257 A1 | 1/2008 | Roychowdhury et al. | |
| 2008/0021438 A1 | 1/2008 | Dacquay et al. | |
| 2008/0027385 A1 | 1/2008 | Freeman et al. | |
| 2008/0033351 A1 | 2/2008 | Trogden et al. | |
| 2008/0071246 A1 | 3/2008 | Nazzaro et al. | |
| 2008/0097390 A1 | 4/2008 | Dacquay et al. | |
| 2008/0103435 A1 | 5/2008 | Graf et al. | |
| 2008/0114373 A1 | 5/2008 | Rathert | |
| 2008/0119761 A1 | 5/2008 | Boecker et al. | |
| 2008/0161726 A1 | 7/2008 | Itou | |
| 2008/0161727 A1 | 7/2008 | Aimi et al. | |
| 2008/0187098 A1 | 8/2008 | Gertner et al. | |
| 2008/0188771 A1 | 8/2008 | Boecker et al. | |
| 2008/0194989 A1 | 8/2008 | Briggs et al. | |
| 2008/0195128 A1 | 8/2008 | Orbay et al. | |
| 2008/0200758 A1 | 8/2008 | Orbay et al. | |
| 2008/0214956 A1 | 9/2008 | Briggs et al. | |
| 2008/0221391 A1 | 9/2008 | Weitzner et al. | |
| 2008/0221392 A1 | 9/2008 | Jorgensen | |
| 2008/0221510 A1 | 9/2008 | Van Der Graaf et al. | |
| 2008/0234668 A1 | 9/2008 | Linnik et al. | |
| 2008/0243176 A1 | 10/2008 | Weitzner et al. | |
| 2008/0262388 A1 | 10/2008 | List et al. | |
| 2008/0269671 A1 | 10/2008 | Lin et al. | |
| 2008/0287831 A1 | 11/2008 | Briggs et al. | |
| 2008/0294068 A1 | 11/2008 | Briggs et al. | |
| 2008/0300444 A1 | 12/2008 | Ye et al. | |
| 2009/0005852 A1 | 1/2009 | Gittings et al. | |
| 2009/0036774 A1 | 2/2009 | Weng et al. | |
| 2009/0036846 A1 | 2/2009 | Dacquay et al. | |
| 2009/0054813 A1 | 2/2009 | Freeman et al. | |
| 2009/0057580 A1 | 3/2009 | Wissman et al. | |
| 2009/0088697 A1 | 4/2009 | Datta et al. | |

FOREIGN PATENT DOCUMENTS

| | | |
|---|---|---|
| EP | 0 447 745 A2 | 9/1991 |
| EP | 0 474 994 A1 | 3/1992 |
| EP | 0 634 947 | 1/1995 |
| EP | 0 541 699 B1 | 5/1996 |
| EP | 1 239 920 | 9/2002 |
| EP | 1 250 900 A2 | 10/2002 |
| EP | 1 286 634 | 3/2003 |
| EP | 0 778 788 B1 | 5/2003 |
| EP | 1 060 765 B1 | 12/2004 |
| EP | 1 485 166 | 12/2004 |
| EP | 1 317 945 B1 | 10/2005 |
| EP | 1 369 143 B1 | 12/2005 |
| EP | 1 060 764 B1 | 3/2006 |
| EP | 0 993 843 B1 | 4/2006 |
| EP | 1 997 532 A1 | 12/2008 |
| FR | 2 764 198 A | 12/1998 |
| GB | 1211316 | 11/1970 |
| GB | 2 449 568 A | 11/2008 |
| JP | 8131453 | 5/1996 |
| JP | 2000-0350742 | 12/2000 |
| RU | 2 089 143 C | 9/1997 |
| RU | 2 325 139 C | 5/2008 |
| WO | WO 88/09677 | 12/1988 |
| WO | WO 93/23110 | 11/1993 |
| WO | WO 96/00099 | 1/1996 |
| WO | WO 98/01179 | 1/1998 |
| WO | WO 98/11936 | 3/1998 |
| WO | WO 00/33916 | 12/1998 |
| WO | WO 99/20337 | 4/1999 |
| WO | WO 99/40869 | 8/1999 |
| WO | WO 99/42162 | 8/1999 |
| WO | WO 99/44686 | 9/1999 |
| WO | WO 99/56825 | 11/1999 |
| WO | WO 00/43066 | 7/2000 |
| WO | WO 01/43825 A1 | 6/2001 |
| WO | WO 01/43826 | 6/2001 |
| WO | WO 01/58523 A1 | 8/2001 |
| WO | WO 01/72202 A2 | 10/2001 |
| WO | WO 02/38199 A2 | 5/2002 |
| WO | WO 02/068052 A1 | 9/2002 |
| WO | WO 02/078785 A2 | 10/2002 |
| WO | WO 03/063944 A2 | 8/2003 |
| WO | WO 20041026106 A2 | 4/2004 |
| WO | WO 2004/053533 A2 | 6/2004 |
| WO | WO 2004/060205 A2 | 7/2004 |
| WO | WO 2004/064916 A2 | 8/2004 |
| WO | WO 2004/098523 A2 | 11/2004 |
| WO | WO 2005/016258 A2 | 2/2005 |
| WO | WO 2005/079294 A2 | 9/2005 |
| WO | WO 2006/031876 A1 | 3/2006 |
| WO | WO 2006/052645 A2 | 5/2006 |
| WO | WO 2006/077242 A1 | 7/2006 |
| WO | WO 2007/027164 A1 | 3/2007 |
| WO | WO 2007/040825 A2 | 4/2007 |
| WO | WO 2007/059208 A2 | 5/2007 |
| WO | WO 2007/134103 A2 | 11/2007 |
| WO | WO 2008/008914 A2 | 1/2008 |
| WO | WO 2008/033426 A1 | 3/2008 |
| WO | WO 2008/045397 A2 | 4/2008 |
| WO | WO 2008/060869 A2 | 5/2008 |
| WO | WO 2008/098251 A1 | 8/2008 |
| WO | WO 2008/106586 A2 | 9/2008 |
| WO | WO 2008/124801 A2 | 10/2008 |

OTHER PUBLICATIONS

Moore, R.F., "Choroidal sarcoma treated by the intraocular insertion of radon seeds", Apr. 1930, The British Journal of Opthalmology, vol. 14, pp. 145-152.

Finger et al., "Palladium-103 Opthalmic Plaque Radiotherapy", Arch Opthalmol-vol. 109 Nov. 1991 (pp. 1610-1613).

Finger at al, "Opthalmic Plaque Radiotherapy for Age-related Macular Degeneration Associated with Subretinal Neovascularization" American Journal of Opthalmology, vol. 127, No. 2, 1999 (pp. 170-177).

Dig. J. Opthalmol., "Development in Retinal Cell Transplants," 2001, vol. 7(2). From: http://www.medscape.com/viewarticle/408963_print.

UIC Office of Technology and Management, "Intraocular Brachytherapy Device," 2003, (2 Pages). From: http://www.vpted.uillinois.edu/Events/iemerging/COAs/BrachytherapvCOA 2.pdf.

Finger et al., "Palladium-103 versus Iodine-125 for Opthalmic Plaque Radiotherapy" Int. J. Radiation Oncology Biol. Phys. vol. 27 (pp. 849-854), 1993.

Official Communication from EPO for Application No. 09 759 334.7, mailed Oct. 10, 2011.

International Search Report and Written Opinion for PCT/US09/046118, mailed Aug. 27, 2009.

HANDHELD RADIATION DELIVERY SYSTEM

CROSS-REFERENCE TO RELATED APPLICATION

This application claims the benefit of the filing date of Provisional Patent Appln. Ser. No. 61/058,737, filed Jun. 4, 2008, the entire contents of which are incorporated by reference herein.

BACKGROUND

The intraocular delivery of ionizing radiation for the treatment of age-related macular degeneration ("AMD") is disclosed in deJuan et al. U.S. Pat. No. 6,875,165, which is incorporated herein by reference. Methods and apparatus for intraocular brachytherapy are disclosed in U.S. Ser. No. 11/559,958, filed Nov. 15, 2006 (2007/0118010), U.S. Ser. No. 11/056,763, filed Feb. 11, 2005 (2005/0277802), U.S. Ser. Nos. 11/228,030, filed Sep. 15, 2005 (2006/0111605), and 11/593,683, filed Nov. 7, 2006 (2007/0055089), which are also incorporated herein by reference. These applications generally disclose a handheld radiation delivery device that houses a radiation source wire ("RSW"). The device includes a cannula adapted to receive the RSW when in the treatment position, and to be inserted into the interior of an eye to deliver ionizing radiation (preferably beta radiation) to a target tissue. The present application is directed to an advanced radiation delivery system suitable for use in the treatment of diseases of the eye, such as AMD, as well as other diseases.

SUMMARY

In accordance with one aspect of the disclosure, an apparatus for the delivery of a radiation treatment source is provided that comprises a first module. A second module is provided that is adapted to be removably associated with the first module. The second module is adapted to receive a radiation treatment source comprising a source wire with a radiation source, such as a radioactive isotope carried at the distal end of the source wire. Preferably, the first module is disposable and the second module is reusable. The apparatus is provided with a cannula that extends from one of either the first module or the second module. The first module is provided with an advancement mechanism that is cooperatively engageable with the second module. The advancement mechanism is operable to advance the radiation treatment source that is disposed within the second module between a first, retracted position, wherein the radiation treatment source is located fully within the second module, and a second, treatment position, wherein the radiation source extends into the cannula and the radiation source is located at a selected position within the cannula.

In keeping with another aspect of the disclosure, the apparatus further comprises a remote actuator, with a flexible umbilicus operatively connecting the remote actuator and the advancement mechanism. Preferably, the umbilicus comprises a push-pull wire that extends between the remote actuator and the advancement mechanism, with the remote actuator being user-operable to allow selective movement of the radiation treatment source between the first and second positions. In a further aspect of the disclosure, the remote actuator includes a damper that retards the rate of movement of the radiation source toward the second position.

In keeping with another aspect of the disclosure, the second module includes a drive mechanism that is cooperative with the advancement mechanism so that when the second module is associated with the first module, the drive mechanism and advancement mechanism cooperate to move the radiation source between the first and second positions. Preferably, the advancement mechanism comprises a movable first driver that is operable to move the radiation treatment source between the first and second positions.

Preferably, the apparatus includes a limiter to limit the number of movements (or cycles) of the radiation source between the first and second positions. The advancement mechanism may also comprise a movable second driver that is operable to advance the limiter incrementally through a pre-selected maximum number of movements of the radioactive source between the first and second positions.

In keeping with another aspect of the disclosure, the drive mechanism of the second module comprises movable third and fourth drivers. The third driver is cooperatively engageable with the radiation source wire and with the first driver of the advancement mechanism when the first and second modules are cooperatively associated, so that movement of the first driver causes movement of the radiation source. The fourth driver is cooperatively engageable with the second driver of the advancement mechanism when the first and second modules are cooperatively associated, so that movement of the second driver causes movement of the fourth driver to incrementally advance the limiter.

In keeping with another aspect of the disclosure, the third and fourth drivers may be provided with retainers to maintain the drivers in the retracted position. The retainers are preferably engageable by the first and second drivers, respectively, so that when the first and second modules are cooperatively associated, the retainers are released and movement of the third and fourth drivers from the retracted position is permitted.

In keeping with another aspect of the disclosure, the limiter is preferably disposed between the housing defined by the first and second modules and the cannula. The limiter advances toward a movement-blocking position with each cycle of the treatment source between the first and second positions. Preferably, the limiter defines a plurality of incremental positions, and is adapted to advance between incremental positions with each cycle of the treatment source between the first and second positions. Preferably, the limiter is also removably attachable to the housing, and, more preferably, the limiter and cannula are an integral assembly that is removably attachable as a unit to the housing. In one aspect of the disclosure, the limiter forms part of a connection assembly with the cannula extending therefrom, the cannula and connection assembly forming a sub-assembly which is preferably disposable.

In keeping with another aspect of the disclosure, the limiter comprises two members, with a second member received in a first member and movable in one direction relative to the first member between a proximal, retracted position and a distal, extended position. The first member is movable in a second, different direction relative to direction of movement of the second member. The first and second members have cooperating surfaces configured so that, as the second member moves in one direction between the proximal and distal positions, the first member moves in the different direction, and the second member is able to move between the proximal and distal positions only a pre-determined number of times before the movement of its cooperating surface is stopped by a cooperating surface of the first member. Preferably, the cooperating surfaces comprise a guide path and a follower disposed to move along the guide path.

In keeping with another aspect of the disclosure, the remote actuator preferably comprises a cable driver disposed within an actuator housing that is movable between first and second positions. A first biaser biases the cable driver to the first position, while a second biaser biases the cable driver to the second position. A selector is provided for selectively permitting the first or second biaser to move the cable driver.

In keeping with another aspect of the disclosure, the cable driver in the remote actuator includes a first driver that is connected to the push-pull cable. A second driver is operatively connected to the first and second biasers, and is movable from a first position to a second position to preload the first and second biasers. Preferably, a member such as a lever is provided for moving the second driver from the first position to the second position, with the selector automatically permitting the second biaser to move the cable driver from the first position to the second position upon preloading the second biaser. A release member or trigger is provided to permit the first biaser to move the cable driver from the second position back to the first position. Preferably, the biasers are constant force springs.

These aspects, as well as other general and specific aspects of the present disclosure, may find application alone or in combination with any one or more of the other aspects mentioned above, as will be apparent upon reference to the accompanying drawings and following detailed description.

BRIEF DESCRIPTION OF THE DRAWINGS

FIGS. 17-21 show the sequence of use of the handheld cable actuator to impart movement to the cable to move the source wire from its storage position to the treatment position.

DETAILED DESCRIPTION

The following description is directed to a specific example of a radiation delivery system and apparatus, and its use. This is by way of illustration, and not limitation, and alternative embodiments will be apparent to those skilled in the art.

In accordance with one aspect of the disclosure, an apparatus for the delivery of a radiation treatment source is provided that comprises a first module. A second module is provided that is adapted to be removably associated with the first module. The second module is adapted to receive a radiation treatment source comprising a source wire with a radiation source, such as a radioactive source, carried at the distal end of the source wire. Preferably, the first module is disposable, while the second module is reusable. The apparatus is provided with a cannula that extends from one of either the first module or the second module.

Figure 1:
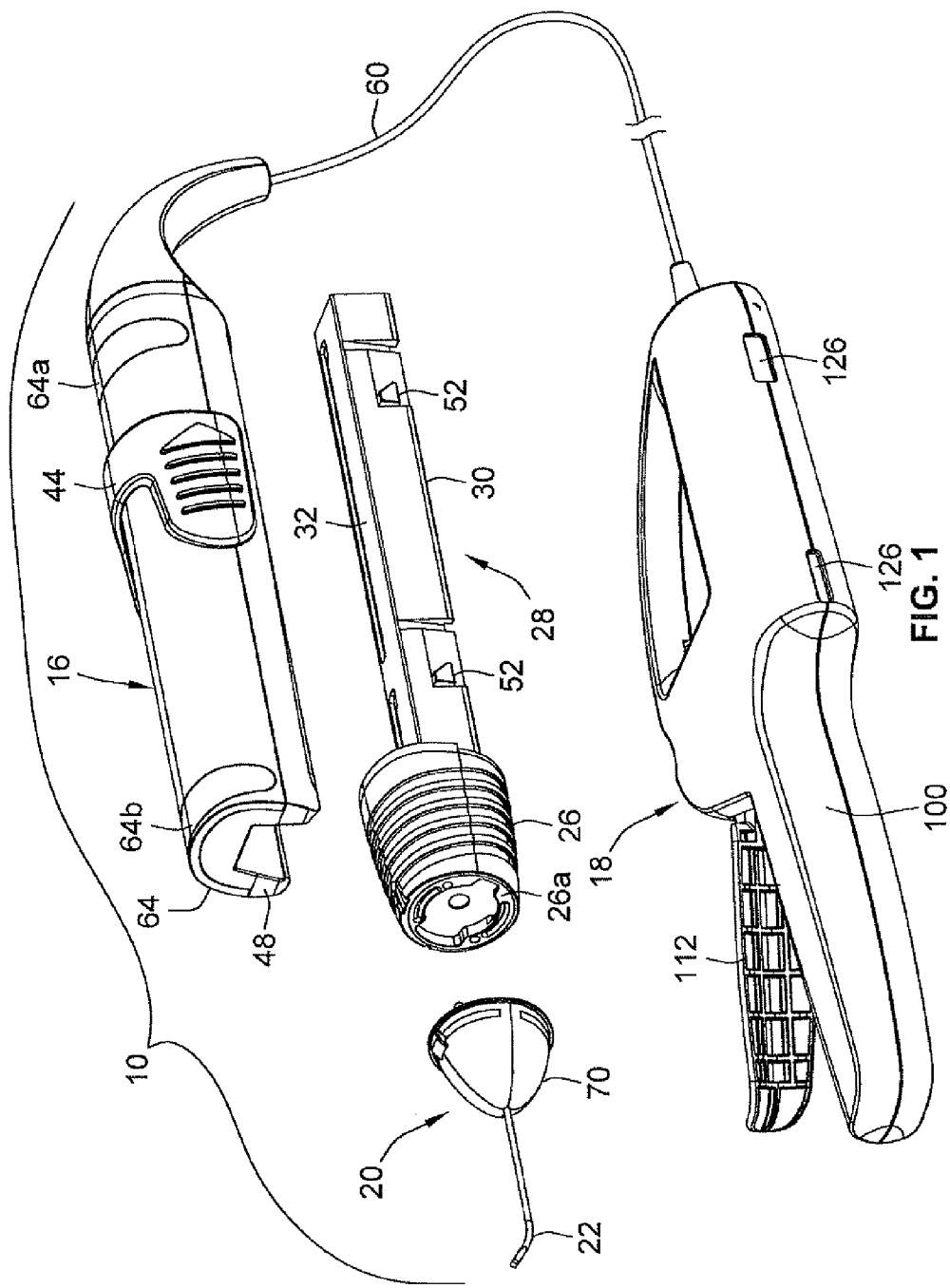
FIG. 1 is a perspective view showing the various components of a radiation delivery apparatus and system according to the present disclosure, including a delivery module comprising at least a reusable portion containing a radioactive source, such as a source wire that terminates in a radioactive element, and a disposable portion including a drive or advancement assembly for moving the radioactive source wire between the treatment and storage positions, a disposable applicator tip including a cannula for receiving the radioactive source wire when in the treatment position, and a remote actuator operatively connected to the disposable portion of the hand piece for imparting motion to the radioactive source.
Figure 2:
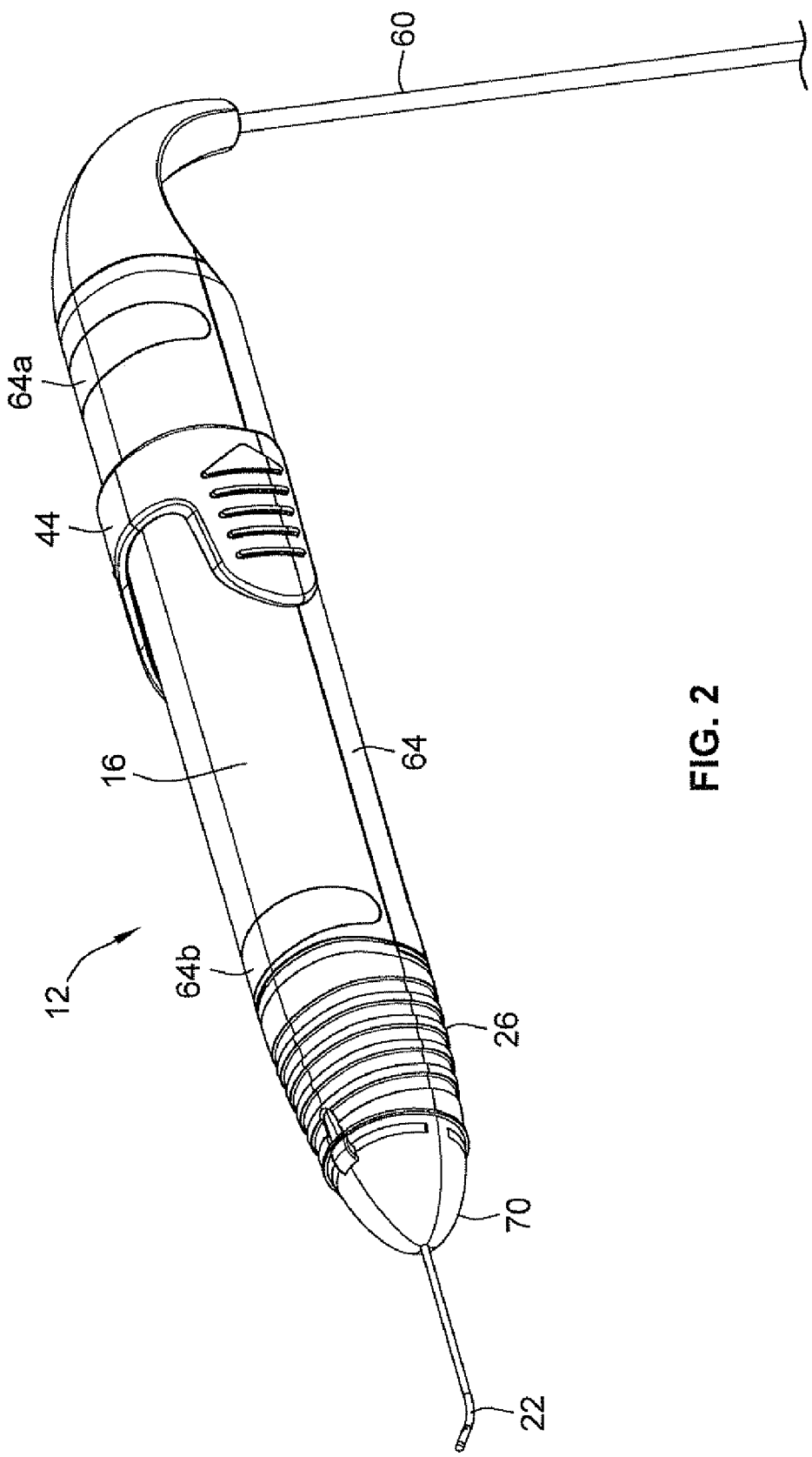
FIG. 2 is a perspective view of the assembled delivery module and applicator tip.

With reference to FIGS. 1 and 2 of the drawings, there is seen a radiation delivery system or apparatus generally designated 10, comprising a delivery module 12 having at least two parts, preferably sized and shaped for use as a hand piece to be easily held by the user. The hand piece 12 comprises a first, reusable part 14 that houses a radioactive source, such as a radiation source wire, or "RSW," tipped with a radioisotope, in its retracted/storage position and a second, disposable part 16 that houses a drive mechanism for moving the RSW between the retracted/storage and the extended/treatment positions. A remote actuator, such as a handheld actuator 18, is operatively connected to the disposable portion 16 of the delivery module 12 to impart motion to the RSW drive mechanism. The actuator 18 is also preferably, not but necessarily, a single use or disposable item. In addition, the distal portion of the hand piece 12 is provided with a disposable applicator tip 20, which includes a cannula 22, that is adapted to be secured to the delivery module 12, the cannula 22 receiving the RSW when it is in the extended/treatment position. As shown, the applicator tip is attachable to the reusable portion 14 of the delivery module 12. However, it could be attachable to the disposable portion 16, assuming sufficient radiation shielding is provided.

Figure 3:
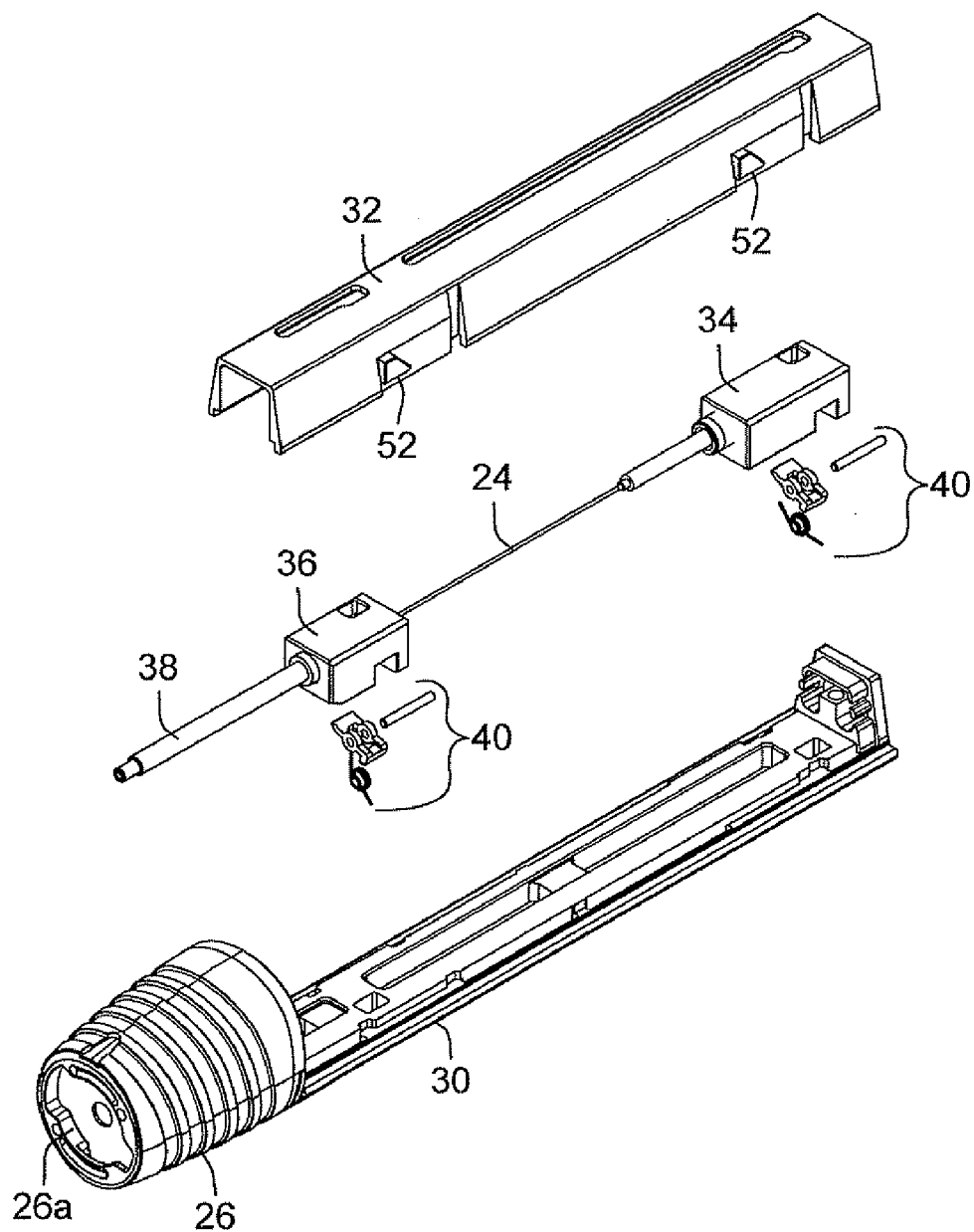
FIG. 3 is an exploded perspective view of the reusable portion of the delivery module, including the radioactive source wire.
Figure 4:
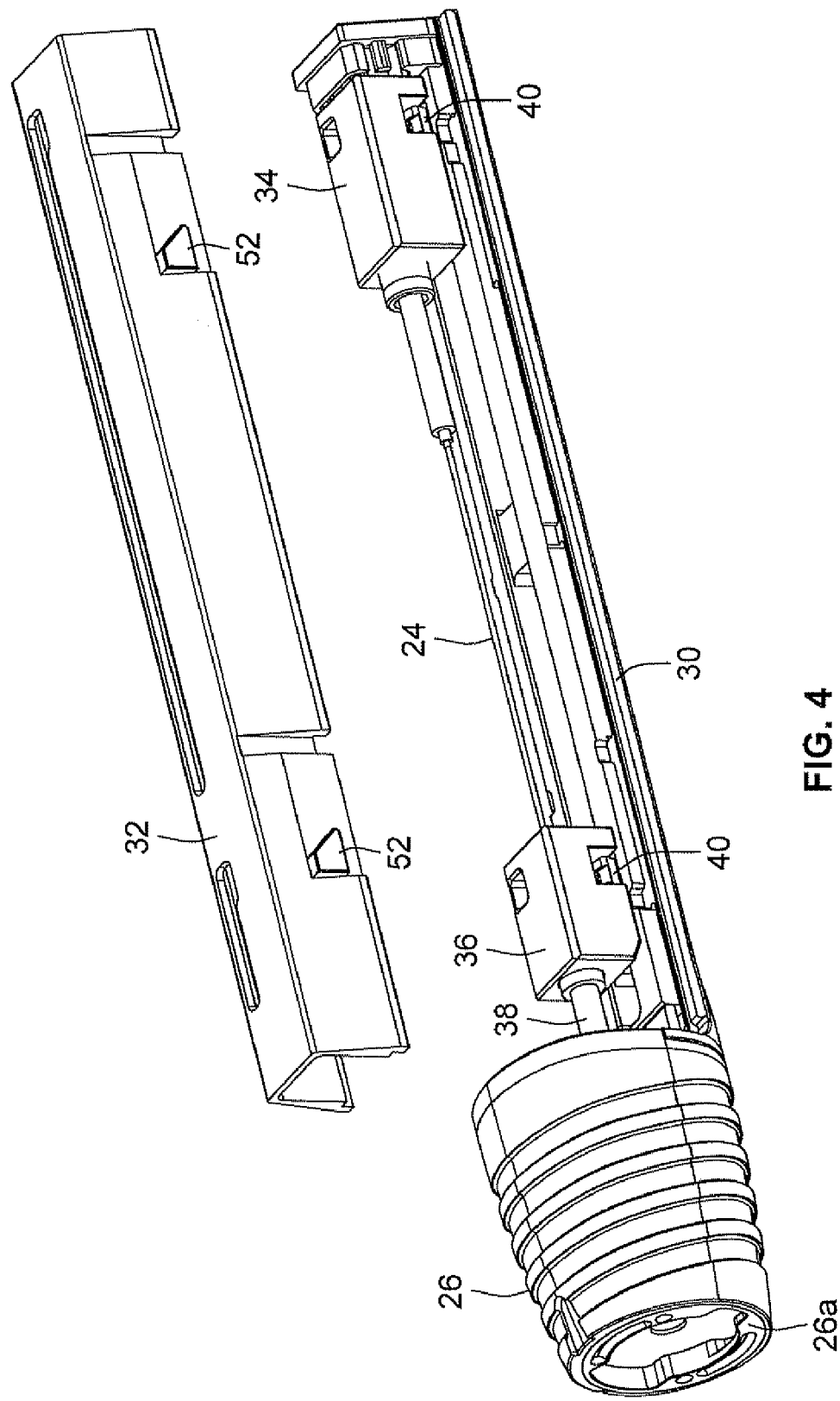
FIG. 4 is a perspective view of the reusable portion of the delivery module with the cover removed to show detail.

With reference to FIGS. 3 and 4, the reusable delivery module 14 is shown in greater detail. The reusable delivery module 14 houses the RSW 24. The RSW 24 preferably comprises a storage canister (not shown), preferably made from stainless steel, at its distal end that contains the radiation source. Preferably a beta-emitting isotope such as strontium 90 or yttrium 90 is utilized, although other types of radiation, such as alpha, gamma, x-ray (including miniature x-ray generators) could also conceivably be used. The stainless steel canister is welded to a stainless steel braided cable, as is generally described in the above-referenced patents.

The delivery module 12 encloses an assembly that mounts the RSW 24 to facilitate its movement between the retracted/storage and extended/treatment positions. The RSW 24 is movable between a retracted/storage position, in which the RSW resides completely within the reusable delivery module 14, and an extended/treatment position, in which the radiation source is located at a selected position in the cannula 22, such as at the distal end or tip. In the retracted/storage position, the distal end of the RSW 24 containing the radiation source resides within a generally cylindrical housing 26 which is made of a material, such as stainless steel, that provides for radiation shielding to limit exposure to radiation such that it preferably remains within acceptable limits. Motion is imparted to the RSW 24 by means of the remote actuator 18 that is operatively connected to the drive mechanism in the disposable delivery module 16, as described in greater detail below.

A lock or locking mechanism is preferably provided for locking the reusable delivery module within the receiving cavity in the disposable delivery module. As illustrated, delivery module 16 includes a slidable latch button 44, which connects to a pair of elongated members 46 received in the bottom housing 48 that include tabs 50. The tabs 50 operate to secure the disposable delivery module 16 to the reusable delivery module 14 by means of the tabs 50 sliding under projections 52 on the cover 32 of the reusable delivery module 14. The elongated members 46 and latch button 44 are biased by springs 52 to the latched position.

In keeping with another aspect of the disclosure, the first, preferably disposable, module is provided with an advancement mechanism that is cooperatively engageable with the second, preferably disposable, module, when mounted thereto. The advancement mechanism is operable to advance the radiation treatment source that is disposed within the second module from a first, retracted position, wherein the radiation treatment source is located fully within the second module, and a second, treatment position, wherein the radiation source extends into the cannula and the radioactive source is located at a selected position within the cannula. The second, preferably reusable, module includes a drive mechanism that cooperates with the advancement mechanism of the first, disposable module so that when the second module is associated with the first module, the drive mechanism and advancement mechanism cooperate to move the radiation source between the first and second positions. Preferably, the advancement mechanism comprises a movable first driver that is operable to move the radiation treatment source between the first and second positions. Preferably, the advancement mechanism also comprises a movable second driver that is operable to advance a limiter incrementally through a pre-selected maximum number of movements of the radioactive source between the first and second positions. The drive mechanism of the second module preferably comprises movable third and fourth drivers. The third driver is cooperatively engageable with the radiation source wire and with the first driver of the advancement mechanism when the first and second modules are cooperatively associated, so that movement of the first driver causes movement of the radiation source. The fourth driver is cooperatively engageable with the second driver of the advancement mechanism when the first and second modules are cooperatively associated, so that movement of the second driver causes movement of the fourth driver to incrementally advance the limiter.

With reference to the drawings, the reusable delivery module 14 comprises a two-part wedge-shaped housing, generally designed 28, extending proximally from the cylindrical housing 26 that includes a base 30 and a cover 32. Together the base 30 and cover 32 enclose the proximal portion of the RSW 24 (when in the retracted/storage position) and define a track along which the RSW moves. The reusable delivery module includes a drive mechanism that includes a RSW driver or driver assembly 34 for moving the RSW between the retracted and extended positions. In the illustrated embodiment, the RSW driver 34 comprises a sliding block for mounting the proximal end of the RSW 24. The drive mechanism also preferably includes a distal driver 36, also comprising a sliding block or pusher (also referred to as the actuator tube drive block 36) that slidingly receives an intermediate portion of the RSW 24. An elongated sleeve or actuator tube 38 extends distally from the distal driver block 36. As described in greater detail below, upon movement of the RSW 24 to the extended/treatment position, the actuator member tube 38 cooperates with the disposable applicator tip 20, which functions as a limiter or limit assembly to limit the number of times the RSW may be advanced into and retracted from the cannula 22.

As noted above, the disposable delivery module 16 includes an advancement mechanism that cooperates with the RSW drive block 34 and the actuator tube drive block 36 to move the source wire between its storage and treatment positions. Upon the delivery of a push force to the drive mechanism, the RSW drive block 34 and the actuator tube drive block 36 move in unison for a first distance (from the positions shown in FIG. 7 to the positions shown in FIG. 8), at which time further movement of the actuator tube drive block 36 is arrested. Thereafter, the RSW drive block 34 continues to move until the RSW 24 reaches its extended/treatment position (as shown in FIG. 9).

Figure 7:
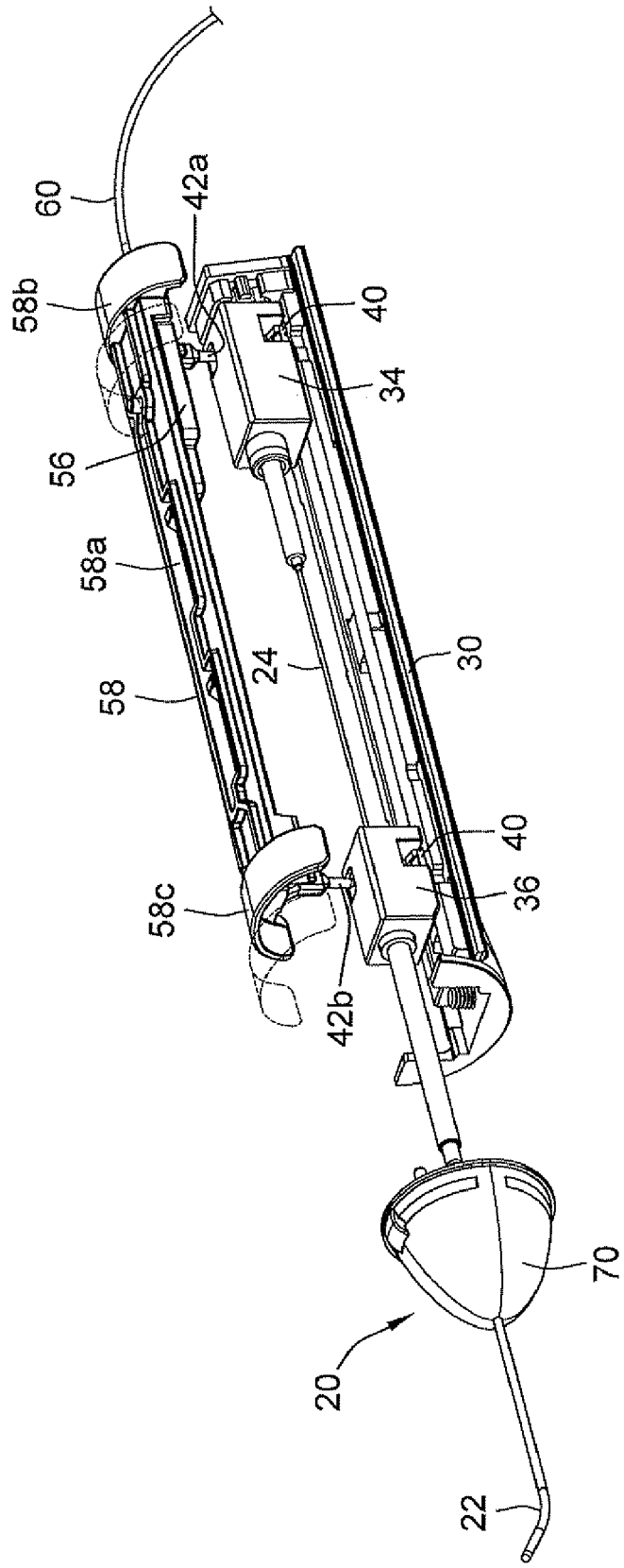
FIGS. 7-9 are exploded perspective views of portions of the reusable delivery module, the disposable part of the delivery module and the applicator tip showing the sequence of movement for advancing the radioactive source wire to the treatment position.
Figure 8:
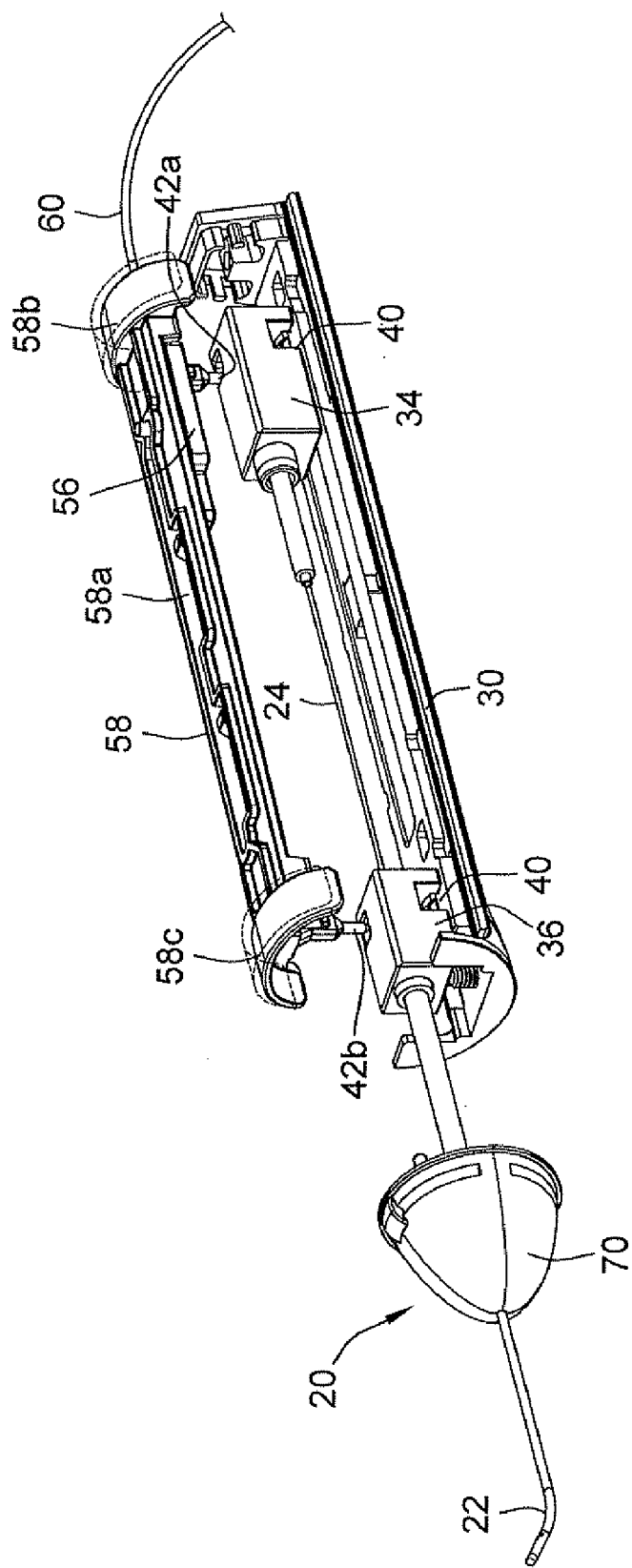
Figure 9:
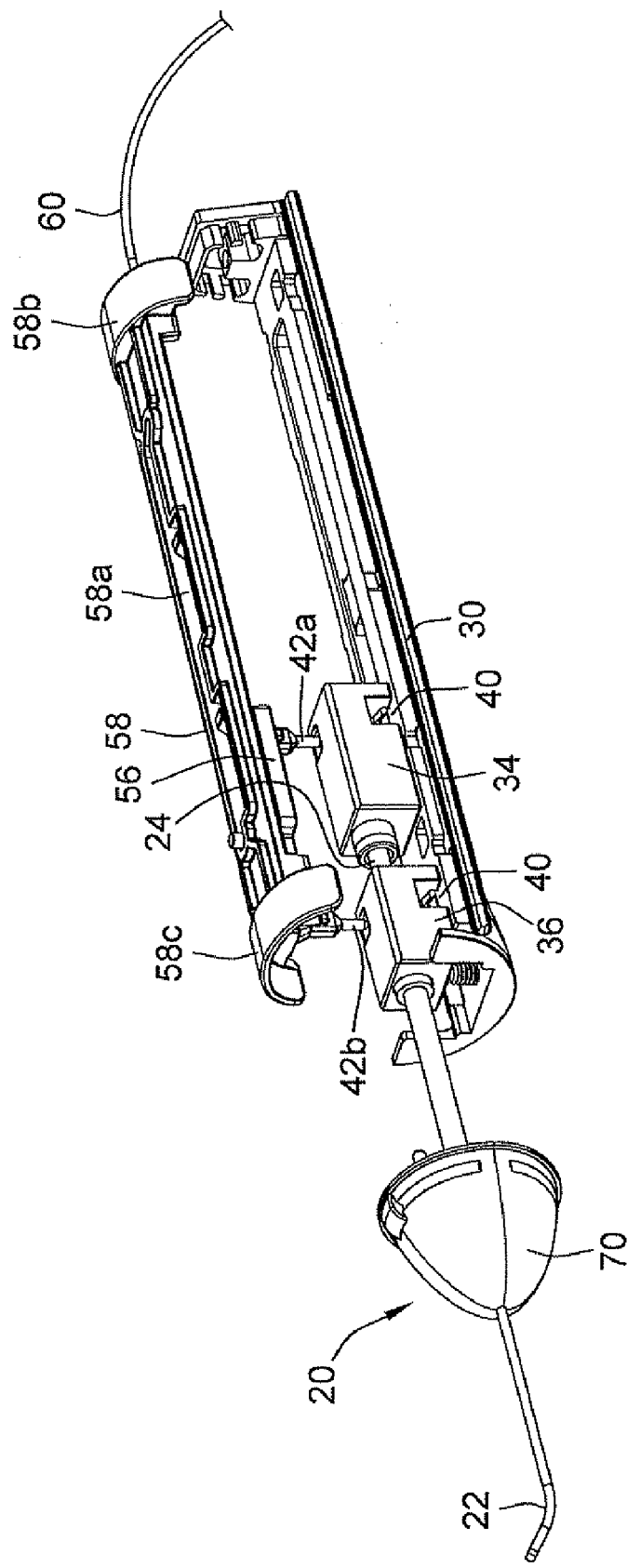

With reference to FIGS. 7-9, the disposable delivery module 16 includes a first driver or drive block 56 from which pin 42a depends to engage the RSW drive block 34 so as to move the RSW drive block 34 between its retracted and extended positions. A second driver or drive block 58 (the actuator drive block) is provided from which pin 42b depends that engages the actuator tube drive block 36 so as to move the actuator tube drive block 36 (and actuator tube 38) between its retracted and extended positions.

The handheld actuator 18 includes an umbilicus 60 connected to the first and second modules. The umbilicus is preferably flexible, which may isolate the hand piece from vibration of the actuator, and provides for transmission of force between the first and second modules, such as by direct mechanical connection, hydraulic, pneumatic or other means of force transmission. As illustrated, the umbilicus 60 comprises a cable housing and a push/pull cable, through which a push/pull force is imparted to the drive block 56 to provide longitudinal movement to the drive block 56. The drive block 56 includes a recessed area 56a that seats a puck 62 so as to permit the puck to slide or translate transversely to the direction of travel of the drive block 56. A pin or post 62a on the puck 62 is received in a guide slot 58a in the actuator drive block 58. The guide slot includes a short, obliquely-oriented section at its proximal end with a long, axially oriented section extending distally therefrom. Upon the initiation of movement of the drive block 56 from the first position (FIG. 7), the pin 62a remains in the obliquely-oriented section of the slot 58a so that both the actuator drive block 58 and the drive block 56 move in unison over a first distance, (from the position shown in FIG. 7 to the position shown in FIG. 8), resulting in the RSW drive block 34 and the actuator tube drive block 36 also moving in unison. When the actuator drive block 58 reaches the position shown in FIG. 8, further movement of the actuator drive block 58 is arrested. The puck 62 then translates laterally in the recessed area 56a, and the pin 62a moves out of the oblique section of the guide slot 58a and along the axial section of the guide slot 58a so that the RSW drive block 34 to continues to move to the fully extended/treatment position (shown in FIG. 9).

In keeping with another aspect of the disclosure, the second and third drivers may be provided with retainers to maintain the drivers in the retracted position. The retainers are engageable respectively by the first and second drivers so that when the first and second modules are cooperatively associated, the retainers are released and movement of the third and fourth drivers from the retracted position is permitted.

Figure 5:
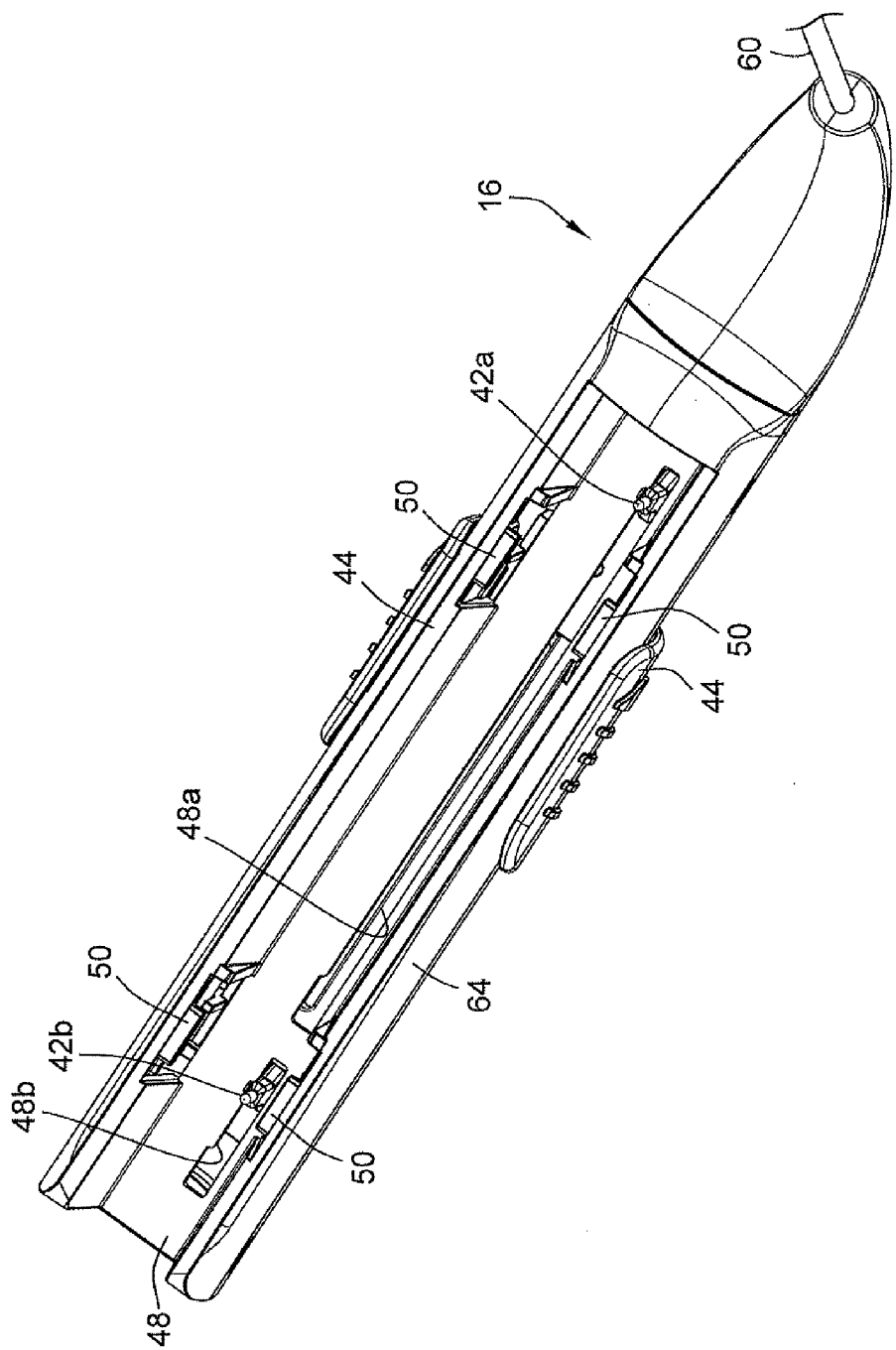
FIG. 5 is a perspective view of the disposable portion of the delivery module showing the surface that interfits with the reusable portion of the delivery module.
Figure 6:
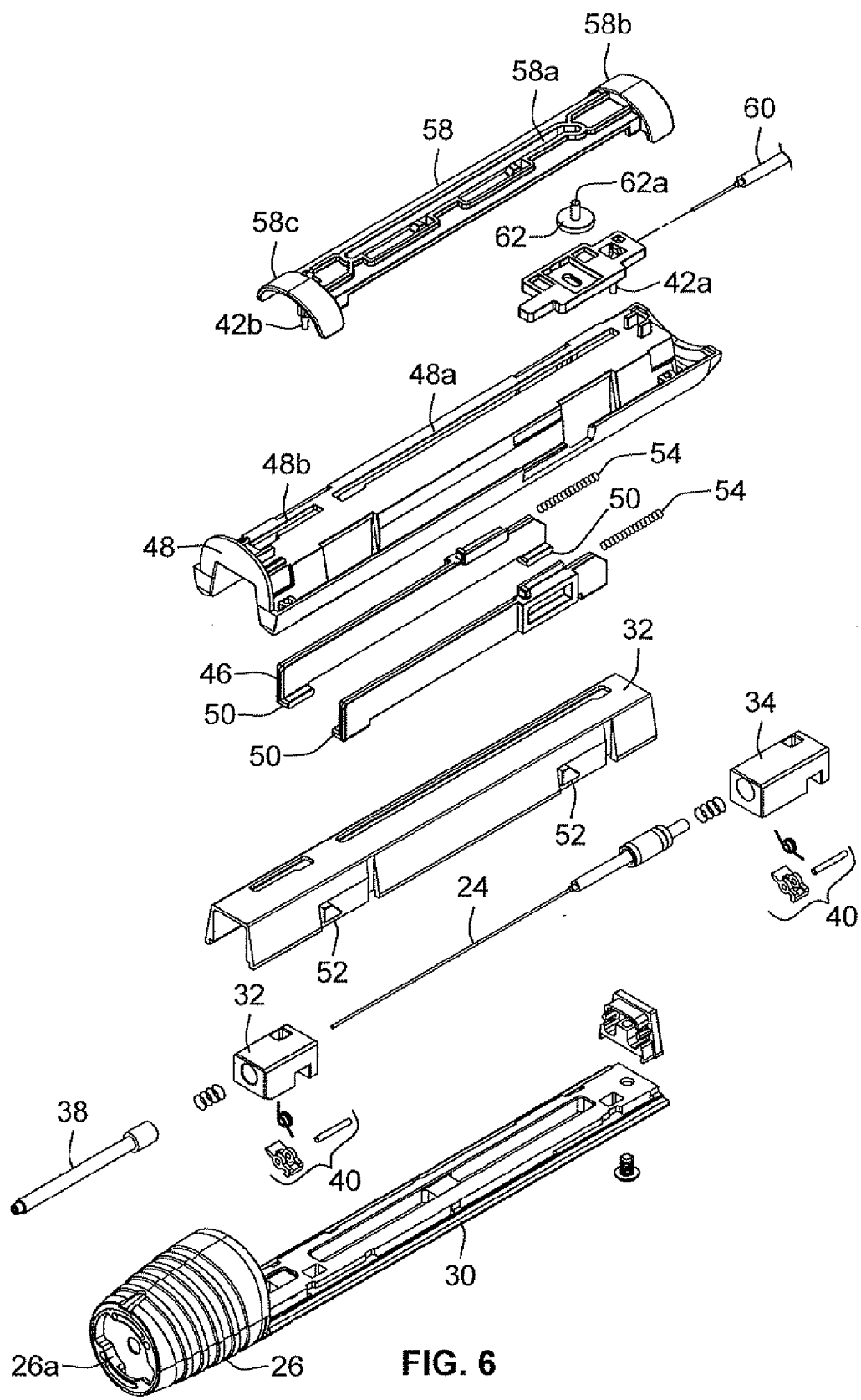
FIG. 6 is an exploded perspective view of the reusable portion of the delivery module and the components of the advancement mechanism for the disposable portion of the delivery module.

With reference to the drawings, both the RSW drive block 34 and the actuator tube drive block 36 preferably include a retainer of any suitable design to maintain the drive blocks in position until the reusable delivery module is attached to the disposable delivery module. As illustrated, spring-loaded latch assemblies 40 are provided that lock their associated drive block in place within the reusable delivery module 14 until attached to the disposable delivery module 16. To this end, the drive system in the disposable delivery module 16 includes pins 42a, 42b (best seen in FIG. 5) that extend through slots 48a, 48b in the bottom wall of housing 48 of the disposable delivery module 16. When the reusable delivery module is received in the disposable delivery module, the pins 42a, 42b are received in the drive blocks 34, 36, respectively, to engage and release the latch assemblies 40.

In keeping with another aspect of the disclosure, visible confirmation of the position of the RSW, namely, whether the RSW is in its retracted/storage position or in its extended/treatment position, is provided. To this end, the upper housing 62 of the disposable delivery module 16 includes proximal and distal windows 62a, 62b, through which proximal and distal indicator surfaces 58b, 58c on the actuator drive block 58 are visible when the RSW 24 is in the retracted/storage and extended/treatment positions, respectively.

In keeping with another aspect of the disclosure, the limiter is preferably disposed between the housing defined by the first and second modules and the cannula. The limiter advances toward a movement-blocking position with each cycle of the treatment source between the first and second positions. Preferably, the limiter defines a plurality of incremental positions, and is adapted to advance between incremental positions with each cycle of the treatment source between the first and second positions. Preferably, the limiter is removably attachable to the housing, and, more preferably, the limiter and cannula are an integral assembly that is removably attachable as a unit to the housing. In one aspect of the disclosure, the limiter forms part of a connection assembly with the cannula extending therefrom, the cannula and connection assembly forming a sub-assembly which is preferably disposable.

Figure 15:
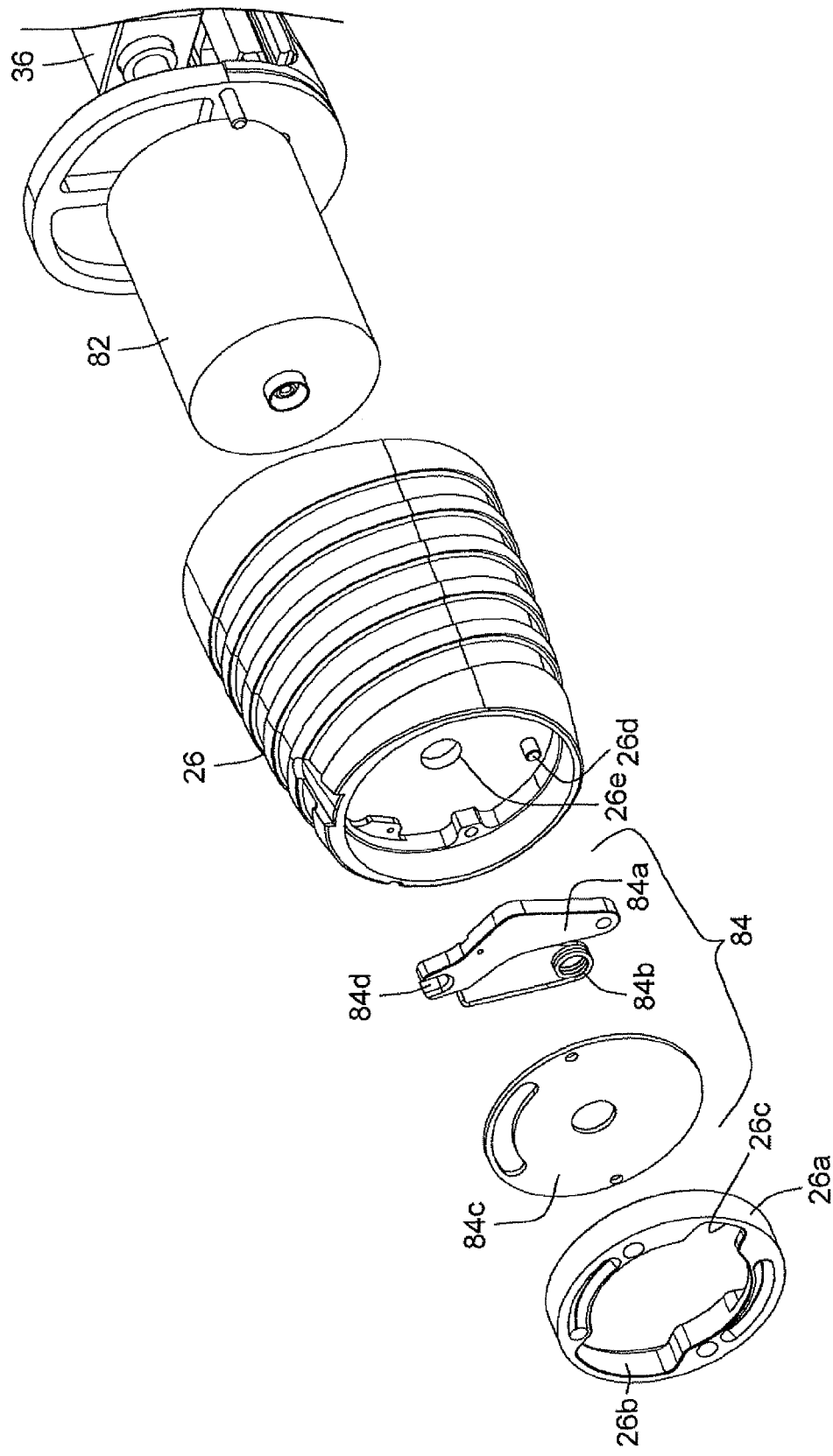
FIG. 15 is an exploded perspective view of the distal end of the reusable delivery module.

Referring to FIGS. 10-14, the applicator tip 20 comprises a cannula 22 mounted to a connection assembly comprising an outer shell or a hub 70 that is removably secured to the cylindrical housing 26 of the reusable delivery module 14 with e.g., a bayonet twist lock. The hub 70 houses a mechanism that limits the number of times that the RSW 24 can be advanced into and retracted from the cannula 22, described in greater detail below. The hub 70 includes an outer sleeve 72 that has flanges 72a, 72b that comprise the male portion of the bayonet lock for removably securing the applicator tip to the reusable delivery module 14. As best seen in FIG. 15, the female portion of the bayonet twist lock is provided by an outer ring 26a that is secured to the interior of the distal end of the cylindrical housing 26 of the reusable delivery module. The outer ring has cutouts 26b, 26c sized and shaped to receive the flanges 72a, 72b. Once the flanges 72a, 72b are positioned through the cutouts 26b, 26c, the applicator tip 20 may be rotated to lock it on to the reusable delivery module 14. The flanges 72a, 72b are preferably of different sizes and shapes to ensure that the applicator tip 20 may be attached to the reusable delivery module 14 in only one orientation. The outer shell 70 of the applicator tip also preferably includes an alignment mark 70a to assist in securing the applicator tip to the reusable delivery module.

In keeping with another aspect of the disclosure, the limiter comprises two members, with a second member received in a first member and movable in one direction relative to the first member between a proximal, retracted position and a distal, extended position. The first member is movable in a second and different direction relative to direction of movement of the second member. The first and second members have cooperating surfaces configured so that, as the second member moves in one direction between the proximal and distal positions, the first member moves in the other direction, and the second member is able to move between the proximal and distal positions only a pre-determined number of times before the movement of its cooperating surface is stopped by the cooperating surface of the first member. Preferably, the cooperating surfaces define a guide path and a follower disposed to move along the guide path.

Figure 10:
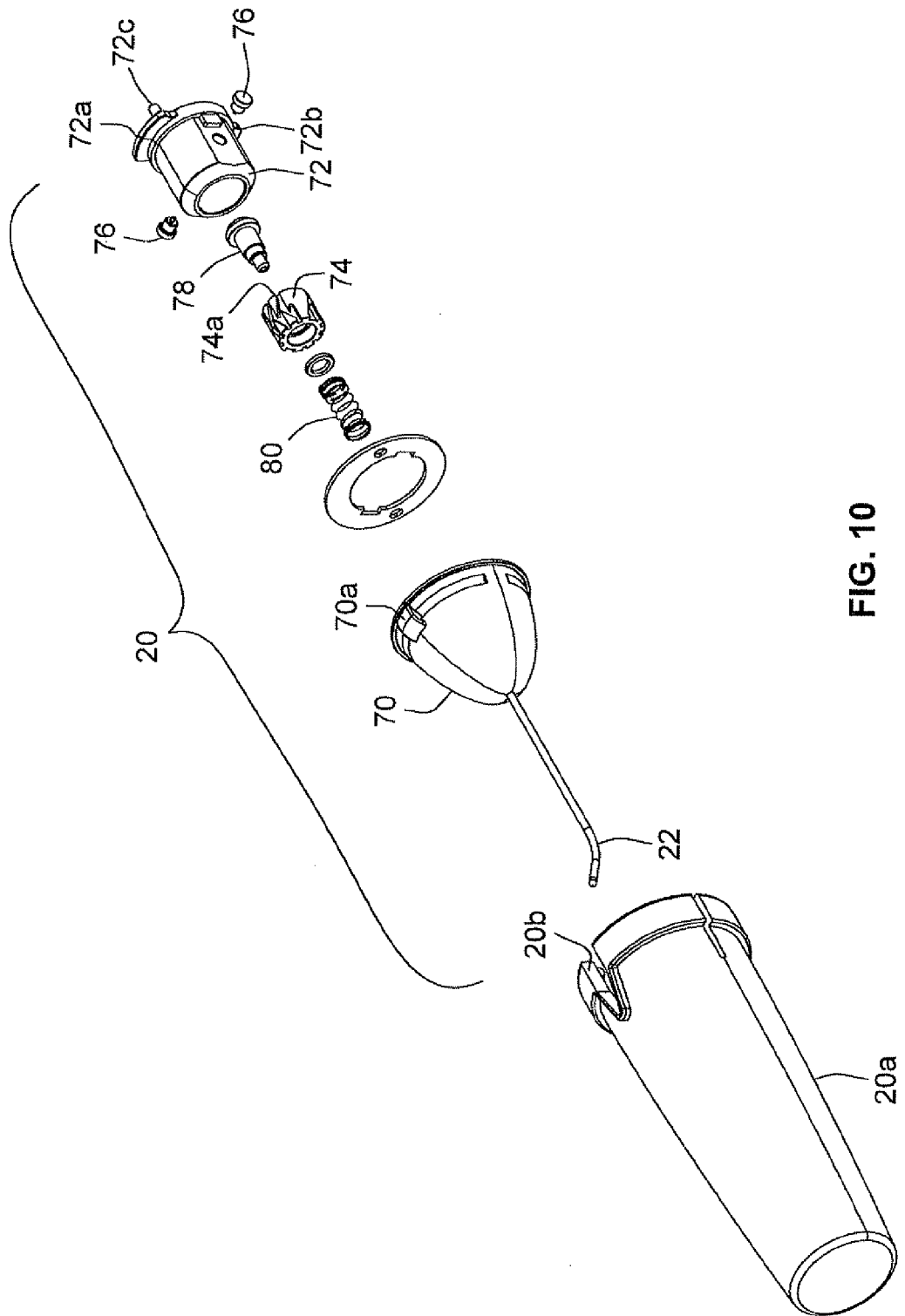
FIG. 10 is an exploded perspective view of the disposable applicator tip.
Figure 11:
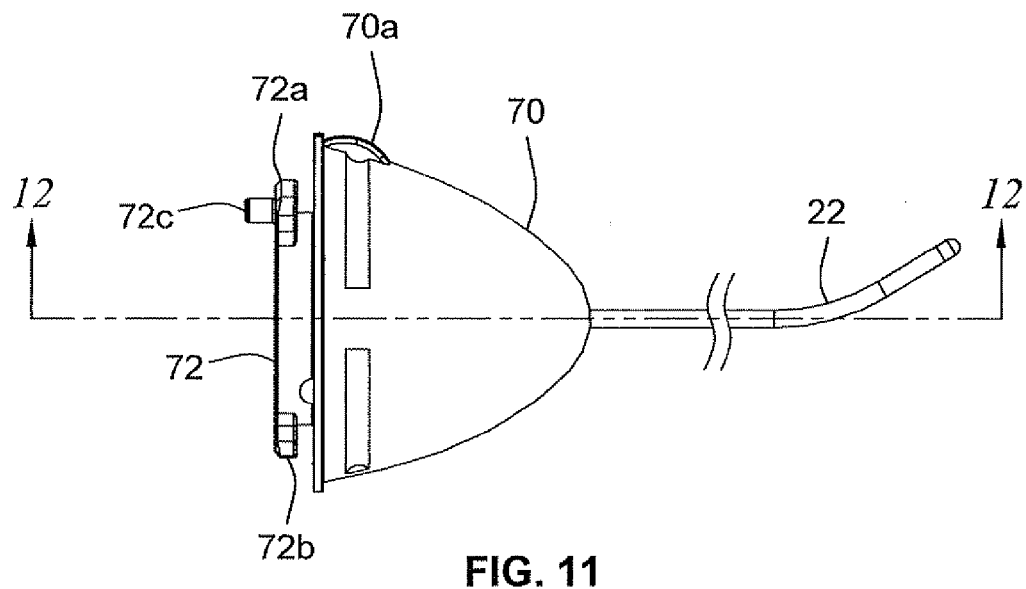
FIG. 11 is a side view of the disposable applicator tip.
Figure 12:
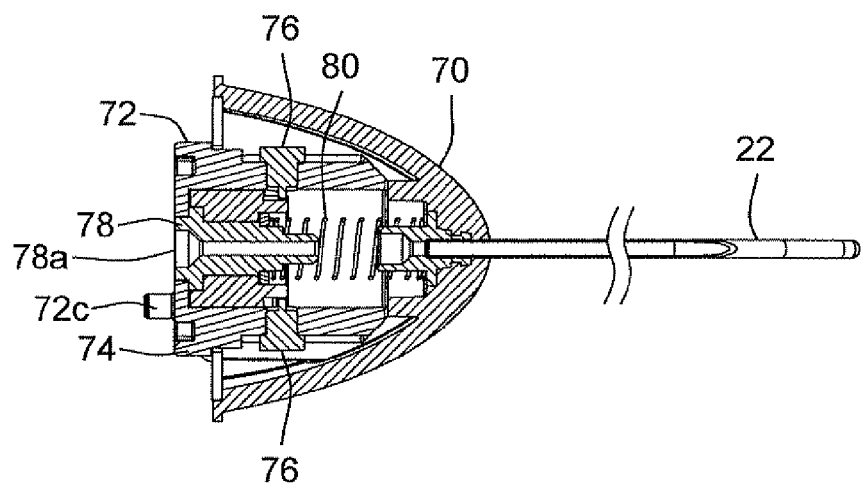
FIG. 12 is a cross-sectional view of the disposable applicator tip taken along line 12-12 in FIG. 11.
Figure 13:
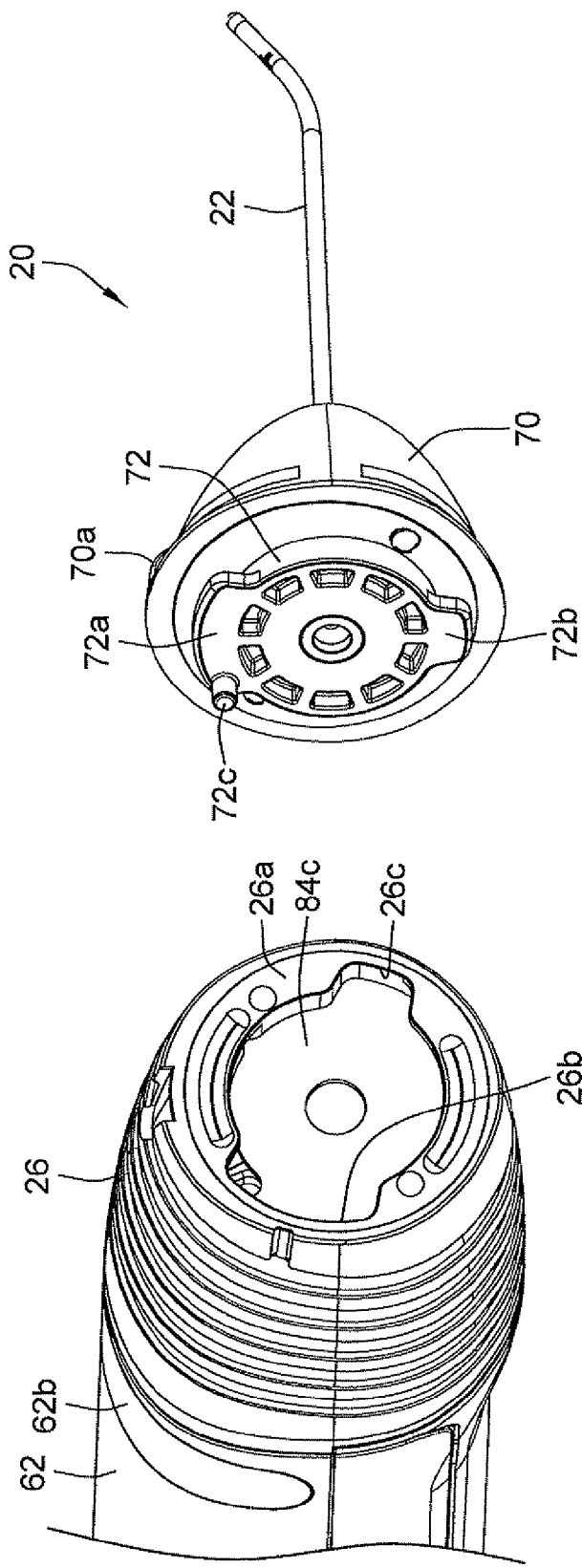
FIGS. 13 and 14 are perspective views of the disposable tip portion and the distal end of the reusable portion of the delivery module showing the interfitting relationship between the two.
Figure 14:
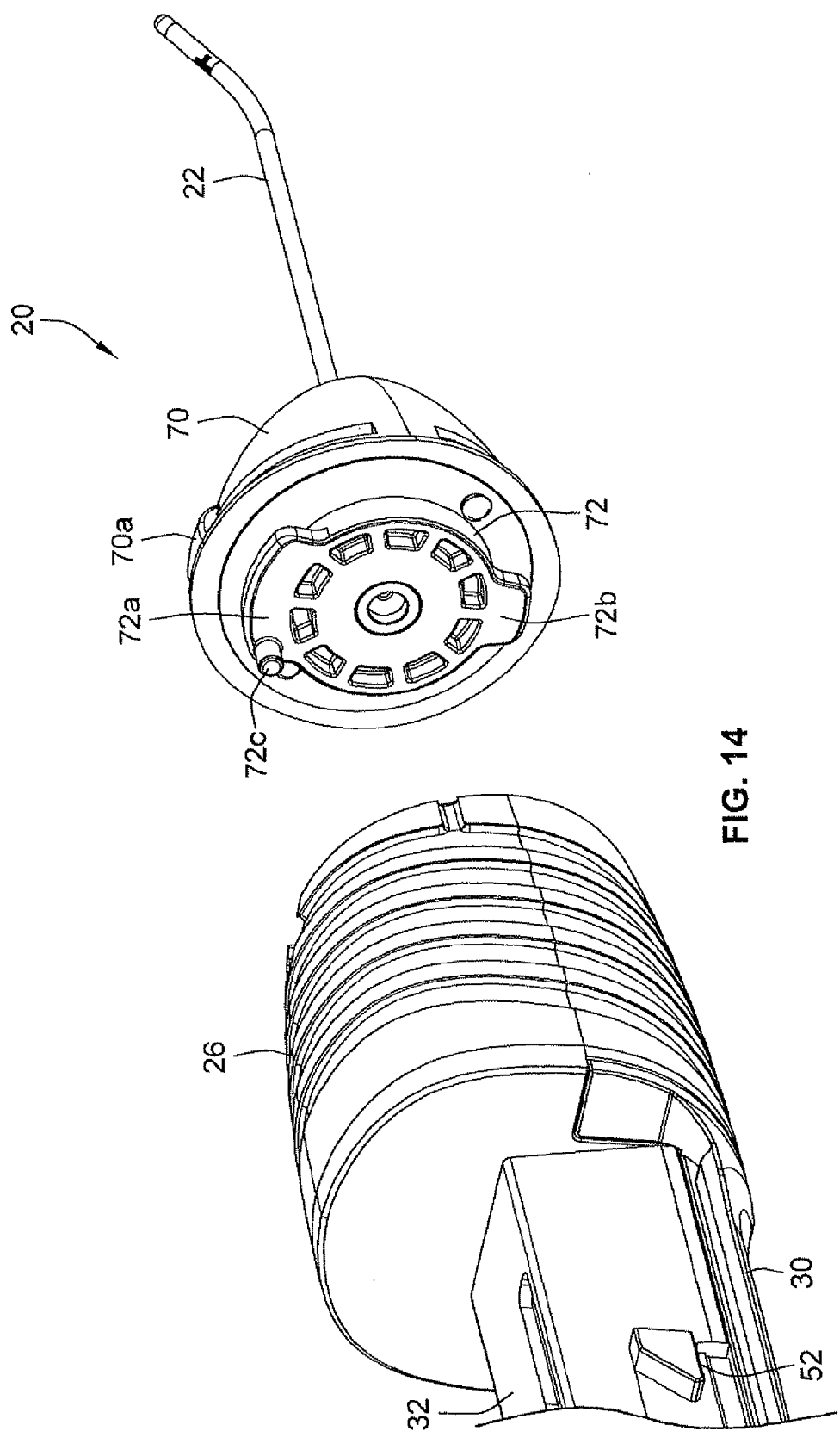

With reference to the FIGS. 10 and 12, the illustrated applicator tip 20 further comprises a sleeve 74 having a guide track 74a on its outer surface is received on the interior of the outer sleeve 72. The guide track sleeve 74 is movable both rationally and longitudinally with respect to the outer sleeve 72 in response to the movement of the actuator tube 38 into and out of the applicator tip 20, which occurs in conjunction with the movement of the RSW 24 into and out of the cannula 22. The guide track 74a provides for a plurality of incremental positions corresponding to a pre-determined number of movements RSW between the retracted and extended positions. In the illustrated embodiment, the guide track 74a has a generally zig-zag or sinusoidal configuration, thus providing an incremental position between each peak and valley in the guide track 74a. The guide track 74a is engaged by guide pins 76 mounted on the outer sleeve 72 (one guide track 74a for each pin 76) so that, as the guide track sleeve 74 moves back and forth longitudinally in response to engagement by the actuator tube 38, the guide track sleeve 74 simultaneously moves rotationally until the guide pins 76 reach the end of the guide track 74a, at which time no further longitudinal movement of the guide track sleeve 74 (or movement of the RSW into the cannula) is permitted.

The guide track sleeve 74 also seats an inner sleeve 78, such that the guide track sleeve 74 is rotatable with respect to the inner sleeve 78. The inner sleeve 78 includes an annular recess 78a that seats the distal end of the actuator tube 38 when the actuator tube 38 is advanced into the applicator tip 20 (as shown in FIG. 8).

A return spring 80 is provided to move the guide track 74 and the inner sleeve 78 back to their initial positions when the RSW is retracted and the actuator tube 38 and actuator tube drive block 36 return to the positions shown in FIG. 7.

Thus, the RSW 24 may be advanced into and retracted from the cannula 22 only a pre-determined number of times before the guide pins 76 reach the end of the guide track 74a on the sleeve 74, and longitudinal movement of the guide track sleeve 74 in response to engagement of the inner sleeve 78 by the actuator tube 38 is arrested. Preferably, four actuations (i.e., extensions and retractions) of the RSW 24 are permitted before the guide track sleeve 74 is precluded from translating axially to its forward position.

Because the reusable delivery module stores the RSW, it is desirable that it be configured so as to reduce the possibility of unintended exposure to radiation during the storage and handling of the device. As noted above, when in the retracted/storage position, the radiation emitter at the distal end of the RSW resides within the cylindrical housing 26 of the reusable delivery module. While the cylindrical housing 26 serves, by itself, to block at least some of the radiation emitted by the RSW, additional shielding may be provided by one or more sleeves received on the inside of the cylindrical housing 26, such as the cylindrical shield 82 (best seen in FIG. 15). The shield 82 is preferably made of a metal having a high density, such as a tungsten alloy, commercially available under the trademark "DENSIMET." Additional shielding may be provided by further cylindrical members within the cylindrical housing 26 that are concentric with the shield 90.

In addition, precautions are desirable to prevent radiation from potentially being emitted out the distal end of the reusable delivery module 14 when the applicator tip is not attached. Consequently, the reusable portion of the hand piece preferably includes a shutter that selectively closes the distal end of the reusable portion to block radiation. As best seen in FIG. 15, the cylindrical housing 26 includes a shutter assembly 84 comprising a shutter plate 84a that is pivotably mounted to a post 26d on the distal face of cylindrical housing 26. The shutter plate 84a is biased by spring 84b so as to cover the aperture 26e through which the RSW 24 must pass in order to move to the extended/treatment position. The shutter assembly 84 also includes a locking plate 84c that substantially encloses the shutter plate 84a and spring 84b. To open the shutter assembly 84, one of the flanges 72a, 72b of the outer sleeve 72 that comprise the bayonet lock includes a pin 72c that, when the disposable tip is mounted to the handpiece, engages a yoke 84d in the shutter 84a. Upon rotation of the applicator tip 20 relative to the reusable delivery module 14 to lock the applicator tip 20 onto the delivery module 14, the shutter plate 84a pivots, and the aperture 26e through which the RSW must pass in order to be introduced into the cannula is opened. Upon removal of the applicator tip 20 from the reusable delivery module 14, the spring 84b pivots the shutter 84a to close the aperture 26e.

In keeping with another aspect of the disclosure, discussed briefly above, the apparatus further comprises a remote actuator, with a flexible umbilicus operatively connecting the remove actuator and the advancement mechanism. Preferably, the umbilicus comprises a push-pull wire that extends between the remote actuator and the advancement mechanism, with the remote actuator being user-operable to allow selective movement of the radiation treatment source between the first and second positions.

With reference to FIGS. 1 and 16-21, the remote actuator 18 is connected to the disposable portion of the handpiece 16 by means of an umbilicus 60 to deliver the force for moving the RSW 24 between the retracted and extended positions. In the illustrated embodiment, the umbilicus 60 comprises a push/pull wire that is moveably received within a cable housing or outer sheath to impart motion to the drive block 56, and thus to the RSW drive block 34 and actuator tube drive block 36, for extending and retracting the RSW and actuator tube. However, other means may be utilized to exert a push/pull force on the drive block 56, such as pneumatic or hydraulic pressure delivered through a fluid lumen, electrical conductors, electromechanical systems, rotary drives, etc., as would be apparent to one skilled in the art.

In keeping with another aspect of the disclosure, the remote actuator preferably comprises a cable driver disposed within a housing that is movable between first and second positions. A first biaser biases the cable driver to the first position, while a second biaser biases the cable driver to the second position. A selector is provided for selectively permitting the first or second biaser to move the cable driver, thereby allowing the user to selectively advance or withdraw the radiation source.

Figure 16:
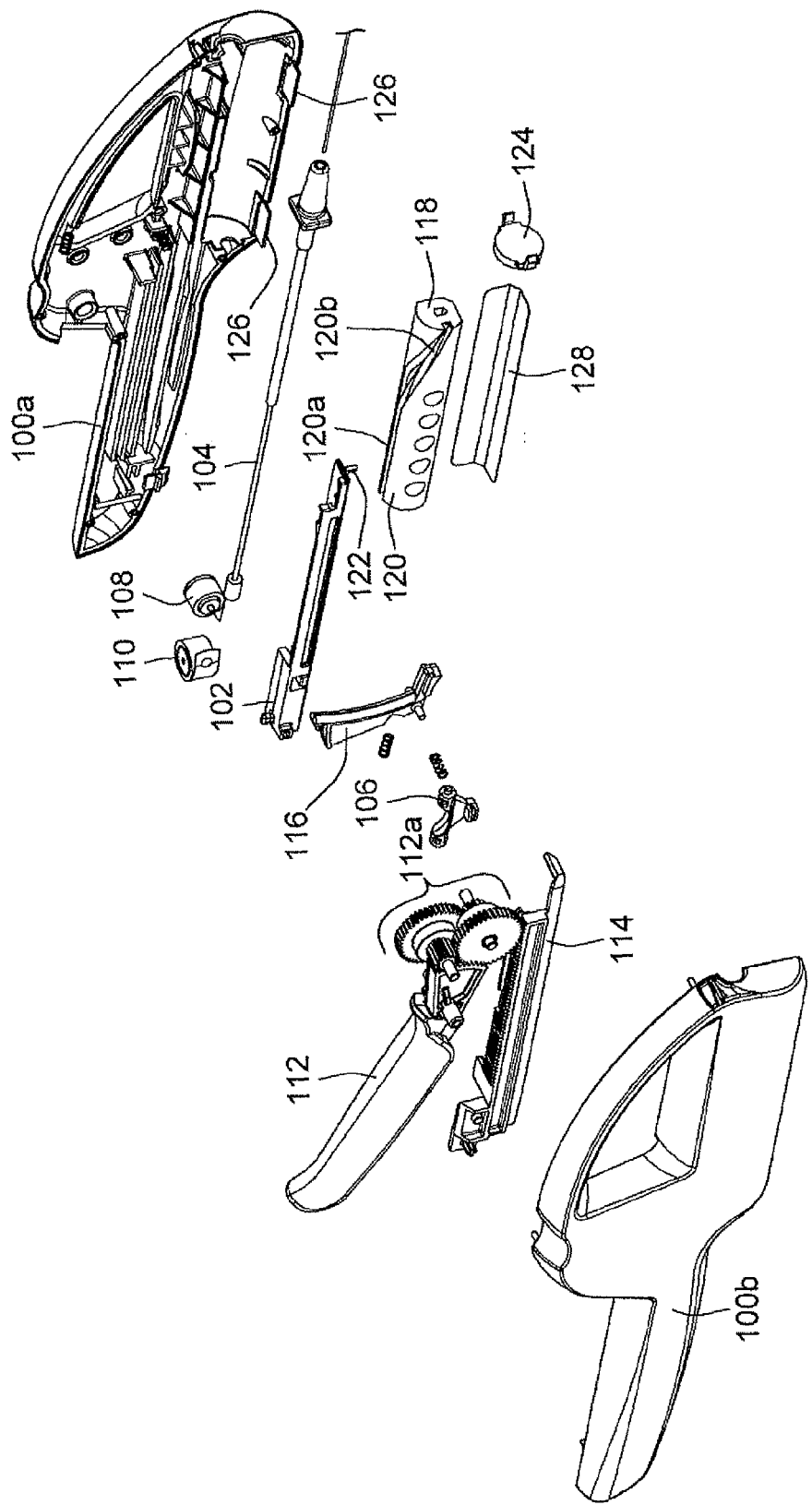
FIGS. 16 and 17 are exploded perspective views of the handheld cable actuator.
Figure 17:
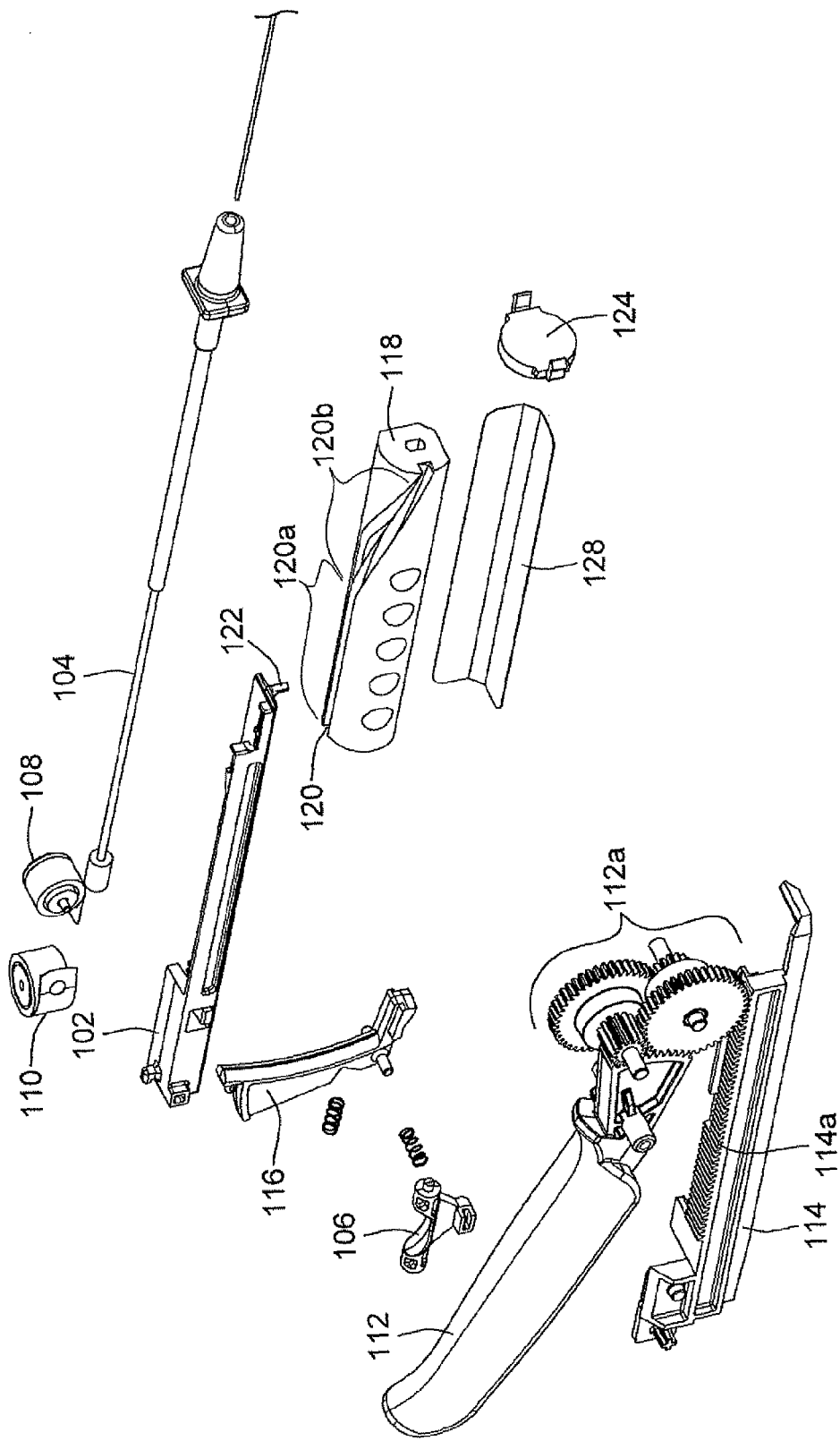

Referring to FIG. 16, the remote actuator 18 comprises a housing having, for example, two halves 100a, 100b, which slidingly mounts a cable block 102 to which the proximal end of a push/pull cable 104 is secured. The cable block 102 is movable within the housing between an initial retracted position (FIG. 18) and an extended position (FIG. 20), and is releasably lockable by a catch 106 in both the extended and retracted positions. The cable block 102 is biased by a first spring 108 to the extended position and is biased by a second spring 110 to the retracted position. As illustrated, the springs 108, 110 are each coiled springs mounted on a spool.

The springs 108, 110 are preloaded by means of an actuator including a lever 112 that, through a series of gears 112a, moves a slider block 114 to unroll the springs. The springs 108, 110 are then selectively released to permit the first or second spring to act on the cable block 102 and move it to and from the extended position. The springs are preferably constant force spool springs so that they move the cable block 102 at a relatively high, constant rate of speed. This ensures that the radiation emitter at the end of the RSW is in transit between the shielded portion of the handpiece and the treatment position for only a short period of time.

Figure 18:
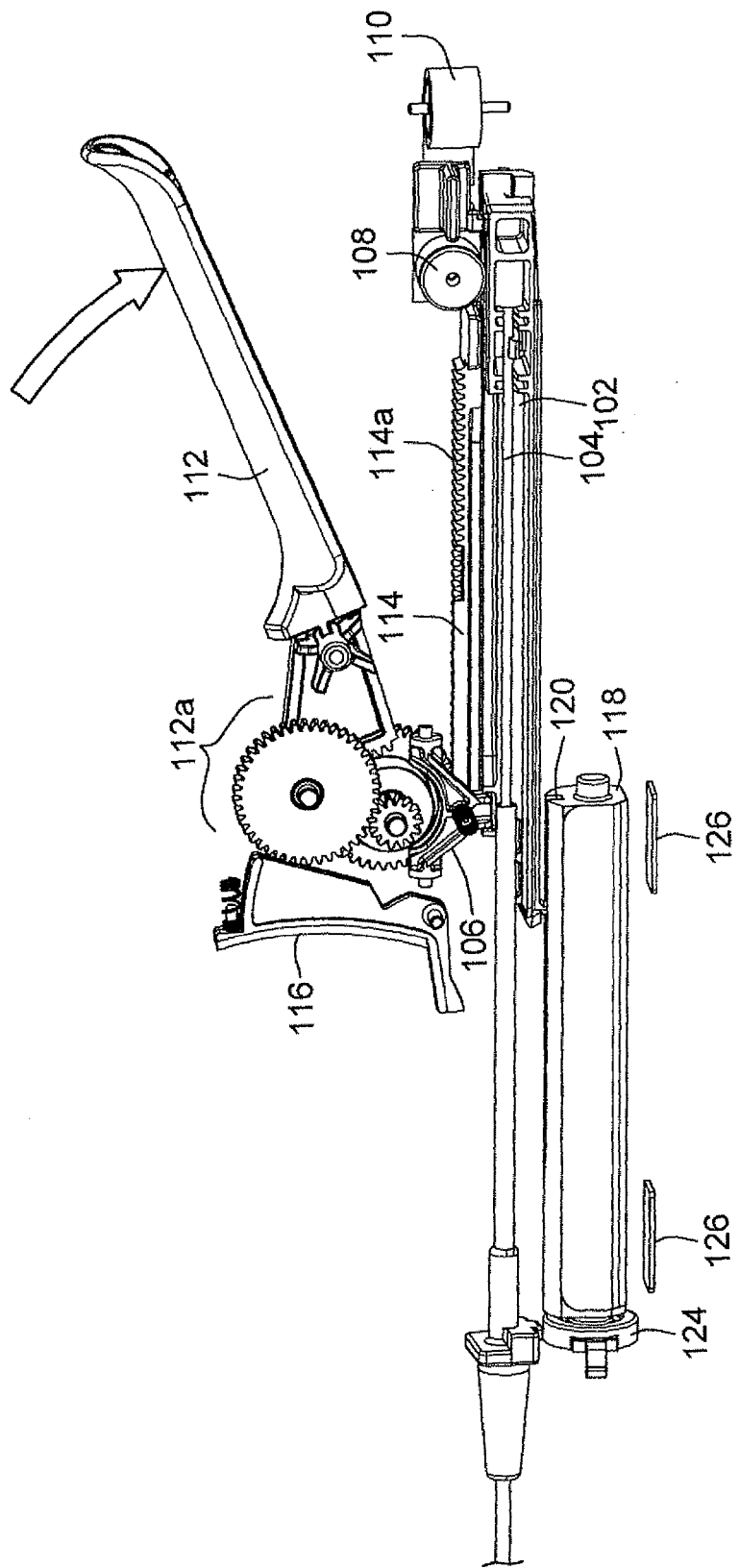
Figure 19:
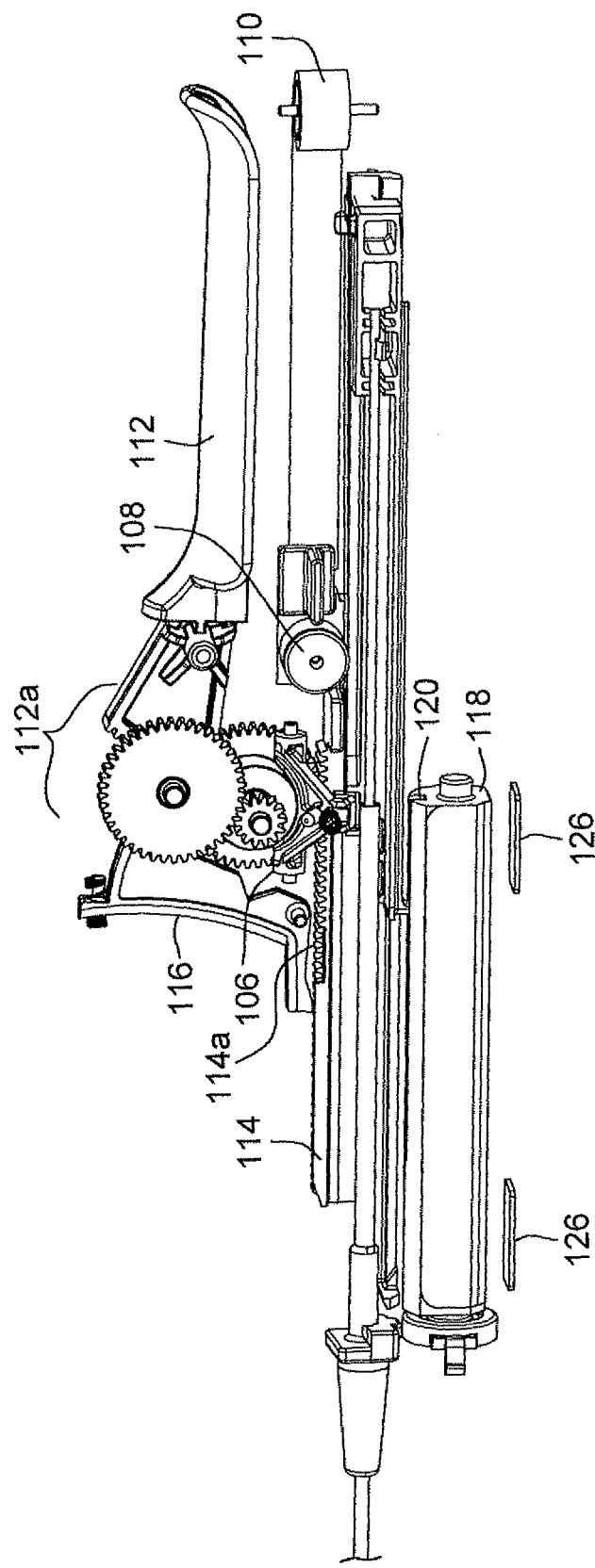
Figure 20:
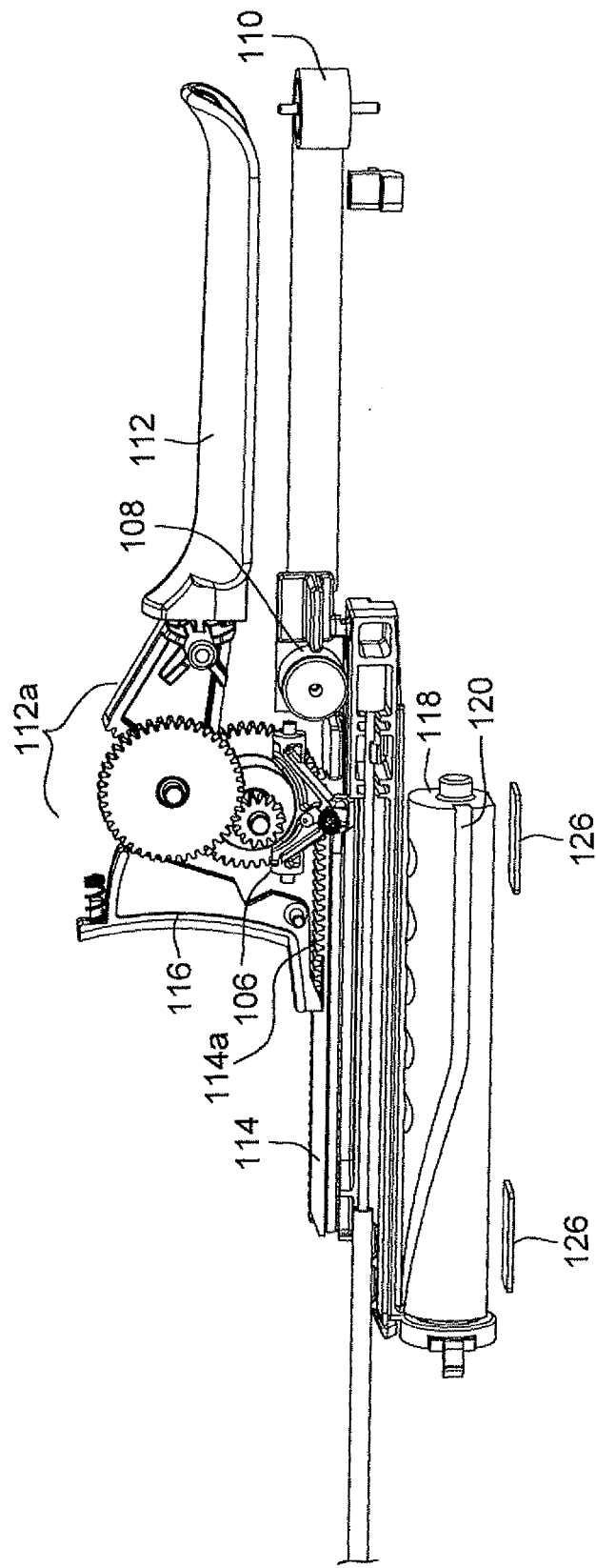
Figure 21:
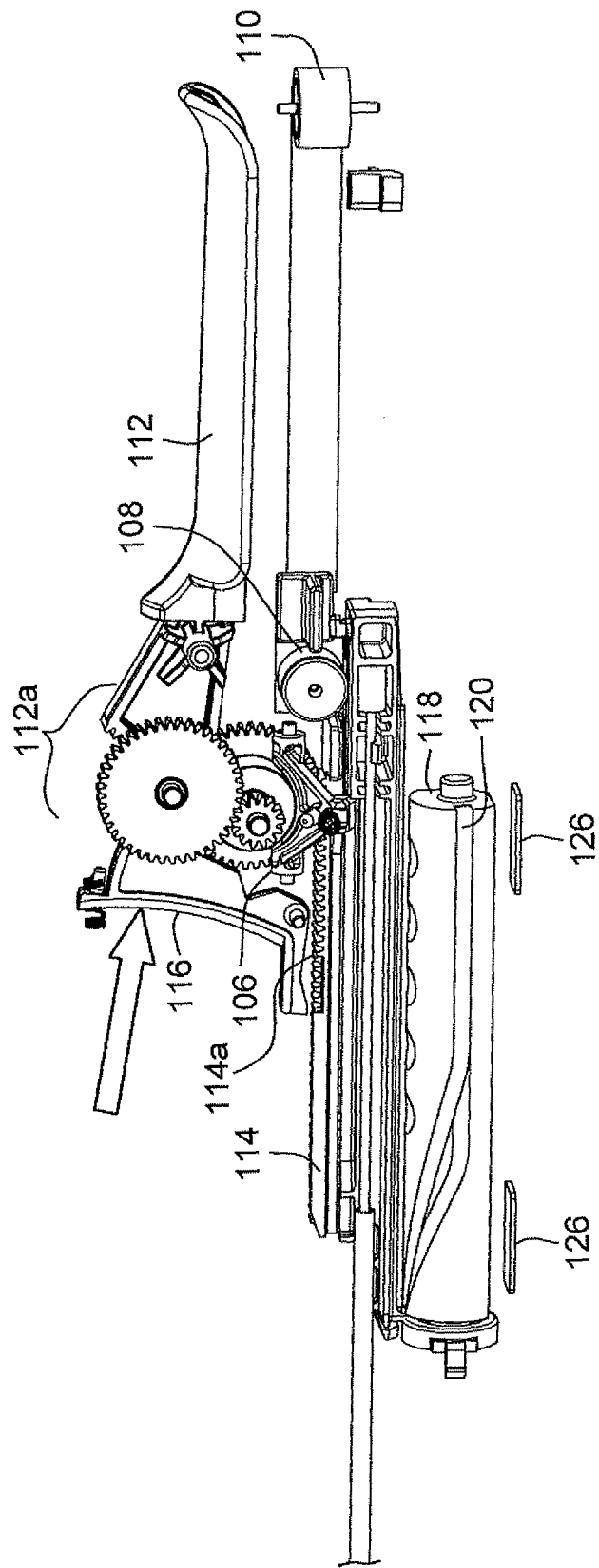

With reference to FIGS. 18 and 19, the springs 108, 110 are preloaded by squeezing the lever 112 so that the gears 112a act on a rack 114a that is integral with the slider block 114 to move the slider block 114 from its first, retracted position (FIG. 18) to its second, extended position (FIG. 19). As the slider block 114 reaches the FIG. 19 position, the catch 106 is released to release the cable block 102 and to allow the stored energy in spring 108 to act on the cable block 102 to move it to the position shown in FIG. 20. When treatment has been effected, and the RSW 24 is to be retracted, a release trigger 116 for the cable block is pulled (as shown in FIG. 21) so that the cable block 102 is released, and the spring 110 returns the cable block 102 to its initial, retracted position.

In keeping with another aspect of the disclosure, the actuator 18 is provided with a damper mechanism that serves to reduce the force with which the RSW 24 reaches its extended position. This, in turn, helps to reduce the forces to which the cannula 22 is subjected upon advancement of the RSW 24 to the treatment position. To this end, the handle 100 for the actuator also houses an elongated barrel member 118 that is mounted for rotation within the handle about its longitudinal axis. The barrel 118 includes a slot or a groove 120 on its outer surface that receives a tab 122 that is integral with the cable block 102. The groove 120 has a first, linear portion 120a and a second helical portion 120b, such that as the tab 122 moves along the groove 120 as the cable block moves from the retracted position to the extended position, the barrel 118 is caused to rotate about its axis as the cable block 102 reaches the extended position. As shown, the helical portion 102b of the slot 102 provides for approximately 90° of rotation of the barrel. The barrel 118 is provided with a rotary damper 124 that resists rotation of the barrel when the tab 122 is moving along the helical portion 120b of the slot 120, thus slowing the movement of the cable block 102 as it moves toward the treatment position, simultaneously with the RSW 24 and radiation source. Of course, various other dampers and damper mechanisms, such as air dampers, piston dampers, and the like, may be operatively connected to the cable block to slow the rate of its movement, and achieve the same effect, as would be apparent to one skilled in the art.

The actuator 18 may also be provided with a position indicator for the cable block 102 to confirm its location in either the retracted position or extended position. To this end, the handle 100 may be provided with one or more windows 126 (two such windows shown) that permit viewing of selected portions of the damper barrel 118. The damper barrel 118 is provided with a color scheme such that a first color (e.g. white) is visible through the viewing windows 126 when the cable block 102 is in the retracted position, and a second color (e.g. black) when the cable block 102 is in the extended position, and the damper barrel 118 has been rotated. In the illustrated embodiment, the damper barrel 118 is provided with a bi-color adhesive label 128 for this purpose.

A brief description of the assembly the system and initiation of treatment follows: The system 10 preferably is assembled in the operating room using sterile technique, without allowing any piece of the system to touch a non-sterile surface. The reusable delivery module 14 is calibrated and sterilized before assembly into the system 10. The reusable delivery module 14 then is attached to the disposable delivery module 16 by snapping it into place so that the tabs 50 associated with the slidable latch button 44 snap over the projections 52 formed on the cover 32 of the reusable delivery module 14.

The applicator tip 20, which is provided with a protective cap 20a (best seen in FIG. 10), is then attached to the delivery module by aligning the marker on hub 70 of the applicator tip, and a notch 20b in the protective cap 20a, with a marking on the delivery module 12. The pieces are pressed together axially, and then the applicator tip is rotated so that the bayonet lock mechanism secures the applicator tip 20 to the delivery module 12. Simultaneously, the shutter plate 34a is pivoted to open the aperture 26e in the cylindrical housing 26 of the reusable delivery module.

At this point, treatment may be initiated, the surgeon having already created an incision in the sclera. The protective cap 20a is removed and cannula 22 is inserted through the incision and positioned in the mid-vitreous cavity, the surgeon viewing the position of the cannula tip 20 through the lens of the eye. With the cannula so positioned, an assistant compresses the advancement lever on the cable actuator. The lever will lock into place and the cable advancement indicator window on the disposable delivery module can be checked to confirm that the radiation source has moved into position in the applicator tip. The assistant can also confirm the position by checking the windows on the actuator that overlie the damper barrel.

The surgeon then moves the device downward until the cannula tip is in the correct position, the cannula tip including a cross hair to assist in its positioning over the area to be treated (i.e., the target tissue). The surgeon then notifies the assistant to begin timing the treatment, and the delivery module is held steady for the entire treatment time for delivery of the designed radiation dose.

Upon completion of a treatment time, the cannula tip is raised with respect to the target tissue back toward the mid-vitreous cavity. An assistant will then press the release trigger on the cable actuator to retract the radiation source. The cable advancement indicator window may be checked again to confirm that the radiation source has been retracted successfully. Again, the assistant may also check the indicator windows on the actuator to confirm. The cannula is then retracted from the eye and the incision closed.

Thus, a radiation delivery system has been described that is suitable for use in the performance of ophthamalic brachytherapy. While the system has been described in terms of a particular embodiment, there is no intent to limit it to the same. Instead, the system is defined by the following claims. Further, the features set forth herein and/or in any one of the claims may be used in combination with any or all of the features set forth herein and/or in the other claims, as would be apparent to those skilled in the art.

The invention claimed is:

1. Apparatus for delivery of a radiation treatment source comprising:
    a first module;
    a second module adapted to be removably associated with the first module and adapted to receive a radiation treatment source comprising a source wire with a radioactive source carried at the distal end of the source wire;
    a cannula extending from one of the first module and the second module;
    an advancement mechanism associated with the first module and cooperatively engageable with the second module, the advancement mechanism being operable to advance a radiation treatment source disposed within the second module from a first, retracted position wherein the radiation treatment source is located fully within the second module and a second, treatment position wherein the radiation treatment source extends into the cannula and the radioactive source is located at a selected position within the cannula
    a remote actuator; and
    a flexible umbilicus operatively connecting the remote actuator and the advancement mechanism, the remote actuator and flexible umbilicus being operable to transmit a force to the advancement mechanism for selective movement of the radiation treatment source between the first and second positions.

2. Apparatus of claim 1 wherein the umbilicus comprises a push-pull wire extending between the remote actuator and the advancement mechanism.

3. Apparatus of claim 1 wherein the remote actuator includes a damper to retard the rate of movement of the radiation source toward the second position.

4. Apparatus of claim 1 wherein the second module includes a drive mechanism cooperative with the advancement mechanism and with a radiation treatment source when disposed within the second module for moving the radiation source between the first and second positions.

5. Apparatus of claim 1 wherein the advancement mechanism comprises a movable first driver operable to move a radiation treatment source between the first and second positions.

6. Apparatus of claim 5 wherein the advancement mechanism comprises a movable second driver and a limiter, the second driver operable to advance the limiter incrementally through a pre-selected maximum number of movements of a radioactive source between first and second positions.

7. Apparatus of claim 1 wherein the first module defines a receiving cavity and the second module is removably insertable into the cavity.

8. Apparatus of claim 7 wherein the first module includes a lock movable between a locked position to lock the second module in the receiving cavity and an open position to allow insertion and removal of the second module.

9. Apparatus of claim 5 wherein the second module includes a movable third driver cooperatively engageable with a radiation source wire and with said first driver when the first and second modules are cooperatively associated, such that movement of the first driver causes movement of the third driver and movement of a radiation source wire.

10. Apparatus of claim 1 wherein the first and second modules provide visible confirmation of at least one of the first or second positions of the radiation source.

11. Apparatus of claim 1, said second module further comprising a passageway for movement of the radiation source between the first and second positions and a movable shutter that closes the passageway unless the cannula is secured to the apparatus.

12. Apparatus of claim 11 wherein said shutter is operable to open the passageway when the cannula is attached to the apparatus.

13. Apparatus of claim 1 further comprising a radiation treatment source wire disposed within the second module.

14. Apparatus of claim 9 wherein said second module includes a retainer associated with the third driver to retain the third driver in a retracted position, the retainer being engageable by the first driver when the first and second modules are cooperatively associated to release the retainer and allow movement of the third driver from the retracted position.

15. Apparatus of claim 6 wherein the second module includes a movable third and fourth drivers;
the third driver being cooperatively engageable with a radiation source wire and with the first driver when the first and second modules are cooperatively associated, such that movement of the first driver causes movement of a radiation source; and
the fourth driver being cooperatively engageable with the second driver when the first and second modules are cooperatively associated, such that movement of the second driver causes movement of the fourth driver to incrementally advance the limiter.

16. Apparatus of claim 15 wherein the second module includes a separate retainer associated with each of the third and fourth drivers to retain the drivers in a retracted position, the retainers being engageable respectively by the first and second drivers when the first and second modules are cooperatively associated to release the retainers and allow movement of the third and fourth drivers from the retracted position.

17. Apparatus of claim 16 on which the first and second drivers are in cooperative engagement to move in unison from the retracted position and to allow continued movement of the first driver after movement of the second driver is arrested.

18. Apparatus of claim 17 wherein said second driver includes a slot including linear portion and an angled portion and said first driver includes an extension that is disposed with the slot, the extension residing within the angled portion during the movement in unison and within the linear portion after the movement of the second driver is arrested.

19. The apparatus of claim 1 including a damper that slows the rate of movement of the radiation source as it moves toward the second position.

20. Radiation source delivery apparatus comprising:
a housing;
a cannula extending from the housing;
a treatment source located within the housing and movable between a first, retracted position within the housing and a second, treatment position within the cannula;
a limiter disposed between housing and the cannula and operable automatically to limit to a pre-determined maximum the number of movements the treatment source can make between the first and second positions.

21. The apparatus of claim 20 wherein the limiter advances toward a movement-blocking position with each cycle of the treatment source between the first and second positions.

22. The apparatus of claim 20 wherein the limiter defines a plurality of incremental positions and is adapted to advance between incremental positions with each cycle of the treatment source between the first and second positions.

23. The apparatus of claim 20 wherein the limiter is removably attachable to the housing.

24. The apparatus of claim 20 wherein the limiter and cannula are an integral assembly removably attachable as a unit to the housing.

25. The apparatus of claim 24 wherein at least a portion of the housing is durable and reusable and the limiter and cannula unit is intended for one time use and disposal thereafter.

26. The apparatus of claim 20 wherein the limiter further comprises:
a first member;
a second member received in the first member and movable in one direction relative to the first member between a first proximal retracted position and a second distal extended position, the first member being movable in a second and different direction relative to direction of movement of the second member;
the first and second members having cooperating surfaces configured so that as the second member moves in one direction between the proximal and distal positions, the first member moves in the other direction, the second member being able to move between the proximal and distal positions a pre-determined number of times before movement of its cooperating surface is stopped by the cooperating surface of the first member.

27. The apparatus of claim 26 wherein one of the cooperating surfaces comprises a surface defining a guide path and the other of the cooperating surfaces comprises a follower disposed to move along the guide path.

28. The assembly of claim 26 wherein the second member is biased toward the proximal position.

29. A disposable radiation treatment apparatus subassembly comprising:
a radiation source housing and a removably attachable connection assembly;
a cannula extending from the connection assembly for receiving a radiation source from the housing through the connection assembly;
the connection assembly including a limit assembly for limiting the maximum number of times that a radiation source can move between the source housing and the cannula.

30. The apparatus of claim 29 in which the limit assembly is advanced toward a limiting position each time a radiation source moves between the connection assembly into the cannula.

31. Treatment source delivery apparatus comprising:
a housing adapted to receive a treatment source;
a cannula extending from the housing;
an advancement assembly located within the housing for moving a treatment source between a first position within the housing and a second position in the cannula;
a remote actuator for actuating the advancement assembly; and
an umbilicus extending between the remote actuator and housing, the umbilicus being in operable communication with the housing and actuator and adapted to transmit a motive force to the advancement assembly for actuating the advancement assembly.

32. The apparatus of claim 31 wherein the umbilicus comprises a push-pull cable.

33. The apparatus of claim 31 wherein the umbilicus comprises an outer sheath and an inner cable.

34. The apparatus of claim 31 wherein the umbilicus comprises force transmission means having one or more of a push or pull drive member, a fluid lumen, a rotary drive member, or an electrical conductor.

35. The apparatus of claim 31 wherein the treatment source comprises a wire and a treatment source carried at the end of the wire and the apparatus further comprises a treatment source module removably receivable within the housing, the source module containing the treatment source and being operably engageable with the advancement assembly in the housing for advancement of the radiation source between the first and second positions.

36. The apparatus of claim 32 wherein the remote actuator further comprises:
a housing;
a cable driver disposed in the housing and movable between first and second positions, a first biaser biasing the cable driver to the first position; a second biaser biasing the cable driver to the second position,
a selector for selectively permitting the first or second biaser to move the cable driver.

37. The apparatus of claim 36 wherein the cable driver further comprises:
a first driver connected to the push-pull cable; and
a second driver operably connected to the first and second biasers and movable from a first position to a second position to preload the first and second biasers.

38. The apparatus of claim 37 further comprising a lever assembly for moving the second driver from the first position to the second position, the selector automatically permitting the second biaser to move the cable driver from the first position upon preloading the second biaser.

39. The apparatus of claim 37 wherein the selector further comprises a release trigger to permit the first biaser to move the cable driver from the second position to the first position.

40. The apparatus of claim 37 wherein the first and second biasers are constant force springs.

41. The apparatus of claim 31 wherein the treatment source emits ionizing radiation.

* * * * *